(12) United States Patent
Jin

(10) Patent No.: US 11,624,724 B2
(45) Date of Patent: Apr. 11, 2023

(54) GAS-BASED METHOD AND DEVICE FOR DIAGNOSING LUNG CANCER USING LIGHT-REGULATED ELECTROCHEMICAL SENSORS

(71) Applicant: QI DIAGNOSTICS LIMITED, Hong Kong (CN)

(72) Inventor: Han Jin, Shanghai (CN)

(73) Assignee: QI DIAGNOSTICS LIMITED, Hong Kong (CN)

( * ) Notice: Subject to any disclaimer, the term of this patent is extended or adjusted under 35 U.S.C. 154(b) by 396 days.

(21) Appl. No.: 16/764,388

(22) PCT Filed: Aug. 31, 2018

(86) PCT No.: PCT/CN2018/103569
§ 371 (c)(1),
(2) Date: May 15, 2020

(87) PCT Pub. No.: WO2019/095790
PCT Pub. Date: May 23, 2019

(65) Prior Publication Data
US 2020/0355644 A1 Nov. 12, 2020

(30) Foreign Application Priority Data
Nov. 16, 2017 (CN) .......................... 201711134128.7

(51) Int. Cl.
*G01N 27/407* (2006.01)
*G01N 27/30* (2006.01)
(Continued)

(52) U.S. Cl.
CPC ....... *G01N 27/4074* (2013.01); *G01N 27/301* (2013.01); *G01N 27/4067* (2013.01);
(Continued)

(58) Field of Classification Search
CPC ............ G01N 27/4074; G01N 27/301; G01N 27/4067; G01N 27/497; G01N 2033/4975; G01N 27/4076
See application file for complete search history.

(56) References Cited

U.S. PATENT DOCUMENTS

| 4,462,890 A | * | 7/1984 | Touda | G01N 27/4071 204/426 |
| 4,481,499 A | * | 11/1984 | Arima | G01N 27/12 73/31.06 |
| 2010/0077840 A1 | * | 4/2010 | Srivastava | G01N 33/0034 356/51 |

FOREIGN PATENT DOCUMENTS

| CN | 103018282 A | * | 4/2013 | ............. G01N 27/00 |
| CN | 106198677 A | * | 12/2016 | ............ G01N 27/407 |
| WO | WO 2010079490 A1 | * | 7/2010 | ............ G01N 33/497 |

OTHER PUBLICATIONS

Liang et al., "Light-Regulated Electrochemical Sensor Array for Efficiently Discriminating Hazardous Gases," ACS Sens. 2017, 2, 1467-1473, including Supplementary information (Year: 2017).*

(Continued)

*Primary Examiner* — Alexander S Noguerola
(74) *Attorney, Agent, or Firm* — Law Offices of Albert Wai-Kit Chan, PLLC

(57) ABSTRACT

The present invention provides methods and devices for detecting and distinguishing various types of gas molecules or volatile organic compounds (VOCs), the methods and devices have enhanced sensing ability; namely response magnitude, sensitivity, detection limit and selectivity (i.e., classification capability). In one embodiment, the present invention provides methods and devices for diagnosing a disease in a subject or a health status of a subject through the detection of VOCs indicative of the disease or health status in question from breath of the subject. In one embodiment, (Continued)

the present invention provides methods and devices for detecting the existence of lung cancer or the stage of lung cancer in a subject through the detection of VOCs indicative of the existence of lung cancer from breath of the subject.

3 Claims, 13 Drawing Sheets

(51) Int. Cl.
*G01N 27/406* (2006.01)
*G01N 33/497* (2006.01)

(52) U.S. Cl.
CPC ....... *G01N 27/4076* (2013.01); *G01N 33/497* (2013.01); *G01N 2033/4975* (2013.01)

(56) References Cited

OTHER PUBLICATIONS

EPO computer-generated English language translation of Jin et al. CN 106198677A, patent published Dec. 7, 2016 (Year: 2016).*
Horzum et al., "VOC sensors based on a metal oxide nanofibrous membrane/QCM system prepared by electrospinning," New J. Chem., 2014, 38, 5761-5768 (Year: 2014).*
Zhou et al., "Highly Enhanced Sensing Properties for ZhO Nanoparticle-Decorated Round-Edged $\alpha$-Fe2O3 Hexahedrons," ACS Appl. Mater. Interfaces 2015, 7, 8743-8749 (Year: 2016).*
EPO computer-generated English language translation of Li et al. CN 103018282A, patent published Apr. 3, 2013 (Year: 2013).*

* cited by examiner

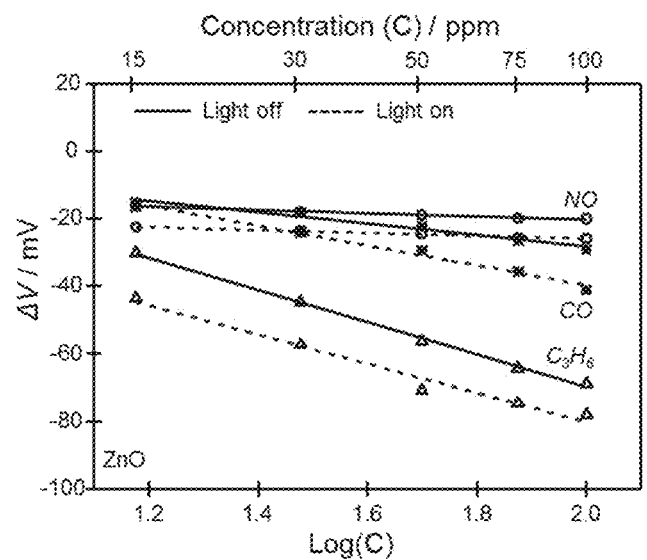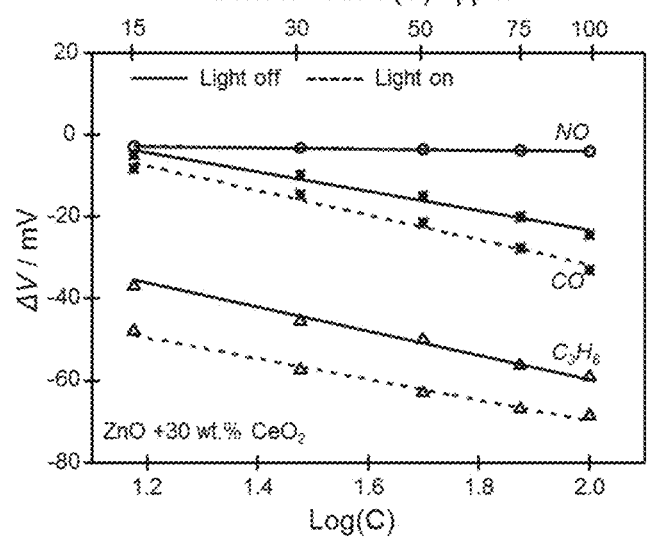

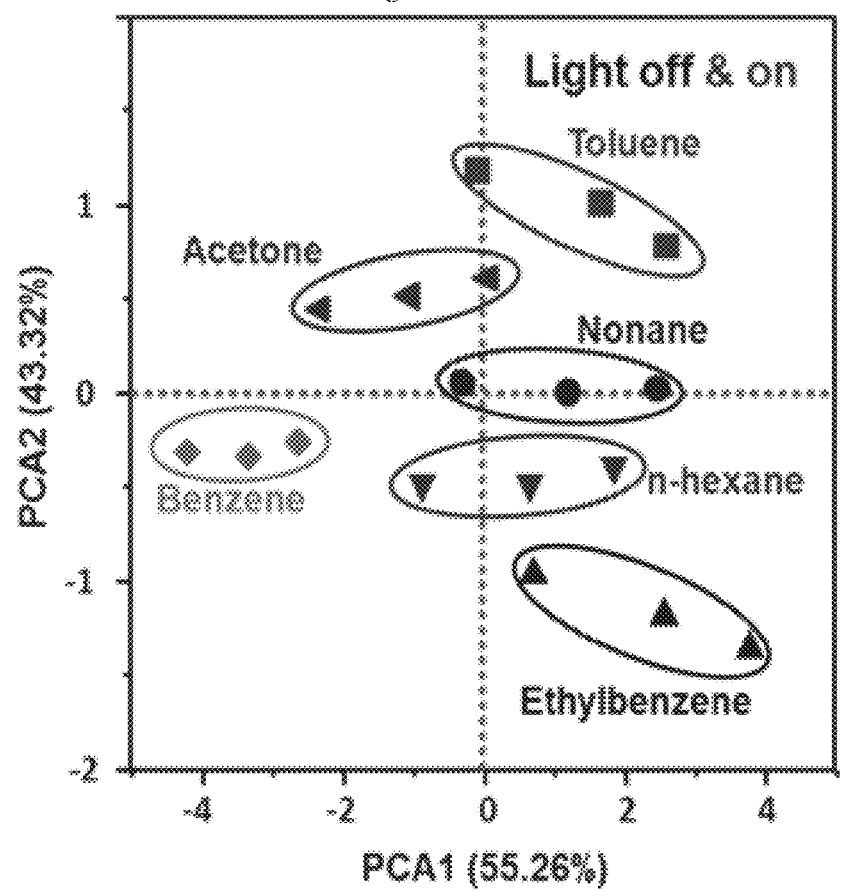

GAS-BASED METHOD AND DEVICE FOR DIAGNOSING LUNG CANCER USING LIGHT-REGULATED ELECTROCHEMICAL SENSORS

CROSS-REFERENCE TO RELATED APPLICATIONS

This application claims the priority of Chinese application no. 201711134128.7, filed Nov. 16, 2017, the entire contents and disclosures of which are hereby incorporated by reference into this application. This application also cites various publications, the entire contents of which are incorporated herein by reference into this application.

FIELD OF THE INVENTION

This invention relates to the gas sensing technology and its application in disease diagnosis. In particular, this invention related to methods and devices for gas sensing and/or disease diagnosis based on gas sensing.

BACKGROUND OF THE INVENTION

Electrochemical gas sensors have been potentially applied in a variety of fields, such as air quality monitoring (1, 2), reducing exhaust gas emission (3, 4) and potential healthcare use (5, 6). This type of gas sensors that comes into many forms, e.g. yttria-stabilized zirconia (YSZ) based (2) and nafion-based (7), gains considerable attention owing to their reliable performance, particularly in harsh conditions (8). It has been reported that part of the electrochemical sensors can even continuously maintain satisfactory sensing performance under high humidity and high temperature 450° C.) environment more than 1200 hours (9), which is rarely reported for other counterparts. However, inadequate detection limit (nominally at dozen of parts per million, ppm level) and unsatisfactory selectivity still severely restrains their wide application (2, 7, 8, 10). To date, several methods have been proposed to enhance the sensitivity and improve the detection limit as well as increase the selectivity, including but not limited to: introducing more electro-active sensing materials (10, 11, 13), fabricating a cascaded sensor array (14) and increasing reaction sites via etching the electrolyte (15, 16). Nevertheless, these methods are time-consuming and inefficient in practice. To improve the sensing performance of electrochemical gas sensors (e.g. YSZ-based electrochemical gas sensors), the present invention studies the effect of illumination on electrochemical gas sensors comprised of photoactive sensing materials (i.e. zinc oxide (ZnO) and ZnO-based composites). While there is no direct evidence in the literature that illumination affects the behavior of these electrochemical gas sensors, a few hints of a potential effect of the UV illumination on those sensors could be deduced from the improved electrocatalytic activity of YSZ-based fuel cells operated under extra light energy (even based on solid-state electrolytes) (17, 18).

Lung cancer accounts for 28% of cancer-related death. Approximately 1.3 million people die worldwide every year. At present, diagnosis of lung cancer very often happens late in the course of the disease since available diagnostic methods are not sufficiently sensitive and specific. It is widely agreed that early diagnosis can prevent lethal and common chronic diseases at an early stage. Prevention of disease at an early stage is receiving more attention and has been considered a cost-effective approach compared with the treatment of disease; it can also lead to better health outcomes. Therefore, there is an urgent need for an inexpensive and minimally invasive technology that would serve as a diagnostic tool, providing efficient early detection of lung cancer and other most concerned diseases.

There is strong evidence suggesting that particulate cancers can be detected by molecular analysis of exhaled air (19). Breath analysis represents a new diagnostic technique that impose almost no risk to patients even if repeated frequently and can provide information beyond conventional analysis of blood and urine. It may even be applied to patients at an intensive care unit or during surgery. Real-time analysis of exhaled breath during an ergometer test or during sleep are also possible. Nowadays, latest advancements in diagnostic frontier are based on volatile organic compounds (VOCs) emanated from disease-related cells, as well as from their micro-environment, at very early stages of the disease. Diseases can be detected using samples from exhaled breath and/or headspace of cells with an artificially intelligent nanoarray consisted of cross-reactive sensors. Air sampling with such sensors is comparably simple, and its results may be interpreted rapidly and automatically, making it suitable for cost-effective screening of large populations.

The feasibility of screening lung cancer at early stage based on VOCs detection primarily relies on two key steps: 1) Development of high-performance VOCs monitoring devices. Although gas chromatography-mass spectrometry (GC/MS) is one of the best methods for detecting low-concentration VOCs, this method is expensive, and the instrumentation is not portable. Inexpensive detectors, such as portable VOC detectors, are preferable for periodic medical inspection and health screening. 2) Informative database containing all VOCs profile that corresponding to each concerned disease. Nevertheless, comprehensive report on the VOCs profile are rarely available at the time of this invention. In sum, breath analysis provides an inexpensive and minimally invasive technology that would serve as a diagnostic tool, allowing efficient and early detection of diseases. However, the lack of high-performance gas sensors and informative database remains the most challenging issues, limiting the clinical applications of this technology.

Herein, the present invention examined the effects of illumination on sensing characteristics of electrochemical gas sensors (e.g. YSZ-based gas sensors); namely response magnitude, sensitivity, detection limit and selectivity (i.e., classification capability) towards gas molecules. The present invention provides electrochemical gas sensors with improved performance as well as devices comprising these improved sensors and uses thereof.

BRIEF DESCRIPTION OF THE DRAWINGS

FIG. 6A depicts the sensing behavior of each sensor part of the sensor array to all the examined gases (in the range of 15-100 ppm), operated with illumination (dotted lines) or without illumination (solid lines). FIG. 6B depicts the response patterns of the electrochemical sensor array in the form of heat map. It can be seen that the response patterns obtained when the sensor array was operated at light off are different from the response patterns obtained when the sensor array was operated at light on. Therefore, by using an identical sensor array comprising three sensor parts, three more disparate response patterns were obtained when illumination was provided to the sensor array. This indicates that classification capability of the sensor array can be improved by providing illumination to the sensor array.

FIGS. 8A-C show the dependence of response signal ($\Delta V$) on the concentration of $C_3H_6$, NO and CO of a sensor array comprising three sensor parts (ZnO, ZnO/30% $Ce_2O_3$, ZnO/20% $Fe_2O_3$) and Mn-based RE, in the range of 15-100 ppm for the sensor array operated with illumination (dotted lines) or without illumination (solid lines).

FIG. 10A-D show the performance of an YSZ-based sensors using various ZnO/$In_2O_3$ composites-SEs (calcined at 900° C.), operated at 425° C., with light off or on. FIGS. 10A-C shows the sensing response to six types of VOCs using ZnO/$In_2O_3$ at various combination. FIG. 10D shows the dependence of the response signal ($\Delta V$) on the concentration of these examined VOCs in the range of 1-4.5 ppm, with light off or light on.

FIGS. 12A-12C show the principal component analysis (PCA) transformation generated by processing three response patterns derived from a sensor array which was solely operated at light off (FIG. 12A); three response patterns derived from a sensor array which was solely operated at light on (FIG. 12B); or (c) six disparate response patterns derived from a sensor array which was operated at light off and light on (FIG. 12C).

DETAILED DESCRIPTION OF THE INVENTION

Figure 1:
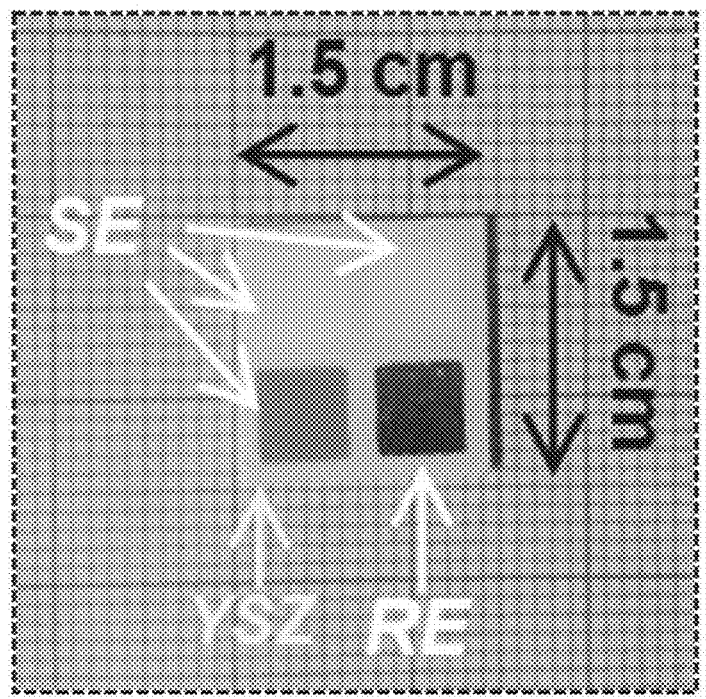
FIG. 1 shows a photograph of the planar YSZ-based electrochemical sensor array. SE refers to sensing electrode while RE refers to reference electrode.

This invention relates to a novel method which essentially and efficiently enhances the sensing ability of solid-state electrochemical gas sensors; namely response magnitude, sensitivity, detection limit and selectivity (i.e., classification capability). In one embodiment, the present invention provides methods and devices for detecting and distinguishing various types of gas molecules or volatile organic compounds (VOCs). In one embodiment, the present invention provides methods and devices for diagnosing a disease in a subject or a health status of a subject through the detection of VOCs indicative of the disease or health status in question from breath of the subject.

In one embodiment, the present invention provides a method for enhancing gas sensing ability of an electrochemical gas sensor. In one embodiment, the present method is capable of efficiently enlarging the response magnitude, enhancing the sensitivity and improving the detection limit of electrochemical gas sensors. In one embodiment, the present method is capable of significantly improving the selectivity (i.e. classification capability) of electrochemical gas sensors in a way that the sensors can detect and differentiate different type of gas molecules or VOCs with higher sensitivity and accuracy.

In one embodiment, the present invention provides methods and devices for detecting the existence of lung cancer in a subject through the detection of VOCs indicative of the existence of lung cancer from breath of the subject.

In one embodiment, the present invention provides methods and devices for diagnosing lung cancer or determining the stage of lung cancer in a subject through the detection of VOCs indicative of the existence or progression of lung cancer from breath of the subject.

In one embodiment, the present invention provides methods and devices for identifying the subtype of lung cancer in a subject having lung cancer through the detection of VOCs indicative of the presence of the subtype of lung cancer in question from breath of the subject.

In one embodiment, the present invention provides a portable and inexpensive VOC detectors for diagnosing lung cancer at early stage. Through operating the electrochemical sensors comprising different combination of photoactive sensing materials (e.g. ZnO-based materials) with illumination, sensing capabilities including but not limited to response magnitude, sensitivity, selectively and detection limit of the electrochemical sensors, such as the YSZ-based electrochemical sensors, are significantly and efficiently enhanced when compared with those of the sensors operated without illumination. In one embodiment, the present invention provides a sensor array operated with illumination (hereinafter denoted as the light-regulated sensor array) that composed of limited number of sensors can identify even more number of targets gases. In one embodiment, the present invention provides an YSZ-based electrochemical sensor array composed of three types of sensors which can detect and differentiate six kinds of VOCs with high sensitivity and accuracy, indicating the feasibility of reducing the number of sensors used in the sensor array while keeping its high performance. In short, the present invention demonstrates an incomparable method in designing future smart electrochemical sensors which is portable and inexpensive while having good performance in gas detection and differentiation, it is expected that the present invention can be applied clinically for early diagnosing various kinds of diseases in a non-invasive way.

Early diagnosis of lung cancer provides a new opportunity for improving lung and systemic health by preventing negative influence results from an organ disorder at the beginning stage. In particular, early diagnosis enables remarkable improvement in survival rate of lung cancer by giving patients timely treatment. In order to establish an easy, simple and non-invasive approach for early diagnosis of lung cancer, the present invention provides a tailor-made artificially intelligent sensor array for lung cancer detection via volatolomics (i.e. analysis of VOCs level in breath sample). The present invention is expected to lead a revolution among medical and hospital professionals as well as at home care in various aspects; for example, the present invention can significantly increase patient compliance, improve curability rate and decrease overall healthcare expenditure. Furthermore, mapping and profiling of air samples originated from breath for signature VOCs in healthy subjects and diseased subjects (e.g. lung cancer patients) by the present invention will enrich the current database of VOC profile which is scarcely reported by other researchers.

The present invention provides a novel and unique light-regulated electrochemical sensor for breath testing which can offer objective diagnostic and monitoring modalities in a field where most clinical diagnoses to date are empiric and based only on the eyesight, skill and experience of the healthcare practitioners. As compared to the current approach such as blood tests, the present invention is non-invasive and does not require a high level of patient compliance. Moreover, by the introduction of a computerized analytic tool, the present invention may revolutionize clinical diagnosis and monitoring of lung cancer by making it simpler, robust and efficient, thereby improving treatment customization and preventing over- or under-treatment.

In one embodiment, the present invention provides a new diagnostic technique for early diagnosis of lung cancer in an easy and non-invasive way. Through mapping the volatile composition of the breath airspace in healthy and diseased subjects, a baseline volatile profile of common organ pathologies is defined and examination of breath VOCs is conducted via artificially intelligent sensor arrays described in this invention. This new diagnostic technique can lead to the creation of a marketable clinical or home-based diagnostic device.

Fabrication of the Sensor Array

In one embodiment, the present invention provide a light-regulated electrochemical sensor array comprising a plurality of photoactive sensing electrodes (SE) and a reference electrode (RE).

In one embodiment, the photoactive sensing electrodes comprise or are essentially made of photoactive metal oxides or photo-catalysts. In one embodiment, the photoactive sensing electrodes comprise or are essentially made of zinc oxide and zinc oxide-based composites, titanium oxide-based composites or photoactive perovskites.

In one embodiment, the reference electrode is essentially comprised of manganese tetroxide ($Mn_3O_4$). In another embodiment, the reference electrode is essentially comprised of platinum (Pt).

In one embodiment, zinc oxide-based composites are composites comprising zinc oxide and another compound (the additive) of varying weight ratio. In one embodiment, zinc oxide-based composites are selected from the group consisting of $ZnO/CeO_2$, $ZnO/Fe_2O_3$ and $ZnO/In_2O_3$. In one embodiment, the weight percentage of the additive in the zinc oxide-based composite ranges from 1% to 50%. In one embodiment, the weight percentage of the additive is 5%, 10%, 15%, 20%, 30%, 40%, 45% or 50%.

In one embodiment, the present electrochemical sensor array comprises at least three photoactive sensing electrodes. In one embodiment, the photoactive sensing electrodes in the same sensor array are comprised of different type of sensing electrodes (e.g. $ZnO/CeO_2$, $ZnO/Fe_2O_3$ and $ZnO/In_2O_3$). In one embodiment, one or more the photoactive sensing electrodes in the same sensor array are comprised of the same type of sensing electrodes (e.g. $ZnO/CeO_2$, $ZnO/Fe_2O_3$ and $ZnO/In_2O_3$) but of different composition.

In one embodiment, the present electrochemical sensor array has the dimension of 5 cm×5 cm×0.2 cm (length×width×thickness).

In one embodiment, the present electrochemical sensor array is prepared by assembling sensing electrodes and reference electrodes through calcination. In one embodiment, the temperature for calcination is ranged from 800-1200° C.

In one embodiment, the present electrochemical sensor array operates and detects gas under illumination. In one embodiment, the present electrochemical sensor array is subject to illumination at the beginning till the end of the detection. In one embodiment, the present electrochemical sensor array is subject to illumination for a period of time during the course of detection. In one embodiment, the present electrochemical sensor array is subject to illumination for 30-60 hours.

In one embodiment, the present electrochemical sensor array is subject to a white light. In one embodiment, the present electrochemical sensor array is subject to an ultraviolet light.

Example 1 provides one embodiment of fabrication of a sensor array for sensing gas molecules such as VOCs. Three zinc-oxide based composites were prepared and used respective for preparing the photoactive sensing electrodes (SEs) of the present electrochemical sensor.

Jin and Haick (6) and Liang et al. (19) described methods fir fabrication of electrochemical sensors and methods for studying the effect of illumination on the sensing behaviors of electrochemical sensors, the entire contents and disclosures of the two references are hereby incorporated by reference into this application.

In one embodiment, the present invention provides a method for improving the gas sensing capability of an electrochemical sensors. The method comprise a step of providing a plurality of sensing electrodes made of different photosensitive and gas sensing materials and a reference electrode, assembling the sensing electrodes and reference electrode, and illuminating sensing electrodes with light. In one embodiment, improvements in gas sensing capability of the electrochemical sensors include but are not limited to the enhancement or improvement in response magnitude, sensitivity and detection limit of the sensor, and improved classification capability after processing all the response patterns obtained from the sensor operated with illumination and without illumination with algorithm.

As used herein, response magnitude refers to the magnitude of response signal generated by a sensor in response to change in a parameter.

As used herein, high sensitivity of a sensor means the sensor can detect a tiny change in a parameter such as a minute change in temperature or concentration of a target molecule. In one embodiment, the present invention provides a sensitive sensor which generate a large response signal in response to a tiny change in concentration of target gas molecules or VOCs.

As used herein, detection limit refers to the lowest value of a parameter a sensor can detect. In one embodiment, the present invention provides a sensor which achieves a lowered detection limit, i.e., the sensor is able to detect target gas molecules or VOCs which exist has a low abundance in the sample.

As used herein, selectivity means the ability to distinguish one class of molecule from another by a sensor. In one embodiment, the present invention provides a sensor has a high selectively and hence a high classification capability since it can detect and differentiate different type of gas molecules and VOCs with higher sensitivity and accuracy. In one embodiment, the present sensor is highly selective or has a high classification capability to target gas molecules since it produces a high response signal to these target gas molecules and negligible signals to other non-target gas molecules.

In one embodiment, the present invention provides a gas sensing device comprising one or more electrochemical sensors described herein. In one embodiment, these electrochemical sensors have improved sensing capability towards gas molecules or VOCs, including improved response magnitude, sensitivity, detection limit and selectivity to gas molecules or VOCs.

In one embodiment, the present invention provides a gas sensing device that can detect gas or VOC at a low concentration. In one embodiment, the present gas sensing device has a detection limit of gas or VOC in the range of about 90 ppb (parts per billion) to about 300 ppb.

In one embodiment, the present invention provides a gas sensing device that can distinguish a plurality of gas molecules or VOCs in a mixture thereof. In one embodiment, the present gas sensing device can distinguish 5-10 different types of gases or VOCs in a mixture. In one embodiment, the present gas sensing device can distinguish 10-20 different types of gases or VOCs in a mixture.

Evaluating of Sensing Behavior of the Sensors

Example 2 describes a method for evaluating the sensing behaviors of the present sensors or sensor arrays. Response to exhaust gases including CO, $C_3H_6$, NO and volatile organic compounds (VOCs) including toluene, nonane, ethylbenzene, n-hexane, benzene and acetone of the sensors were investigated in order to evaluate the gas sensing characteristics of these sensors.

To study the effect of illumination on gas sensing, the gas sensing characteristics of sensor arrays comprising different combination of sensor parts or individual sensor parts were evaluated with and without illumination and it was discovered that illumination could improve the gas sensing performance including response magnitude, sensitivity, selectivity (i.e., classification capability) and detection limit of the tested sensor parts in respect to certain gas species.

A) Sensing Behavior of the Light-Regulated Electrochemical Sensor Array to Exhaust Gases (CO, $C_3H_6$, NO)

Initially, calcination and operational temperature for the sensor part utilizing ZnO-SE and Mn-based RE were optimized.

Figure 2:
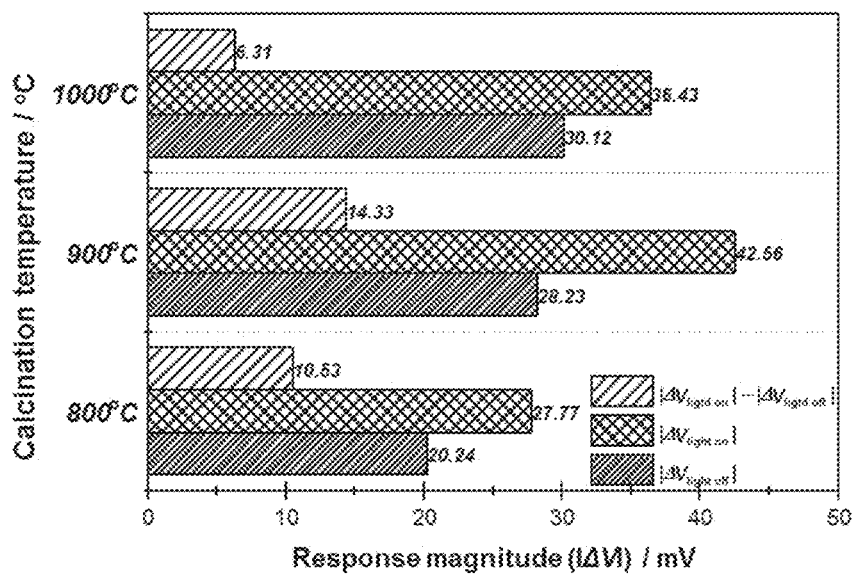
FIG. 2 shows the response magnitude in terms of change in voltage ($\Delta V$) to $C_3H_6$ (15 ppm) for a sensor part using zinc oxide sensing electrode (ZnO-SE) (calcined at 800, 900, or 1000° C., with the intervals of 200° C.) and Mn-based reference electrode (Mn-RE), operated at 450° C., with illumination (light on) and without illumination (light oft).
Figure 3:
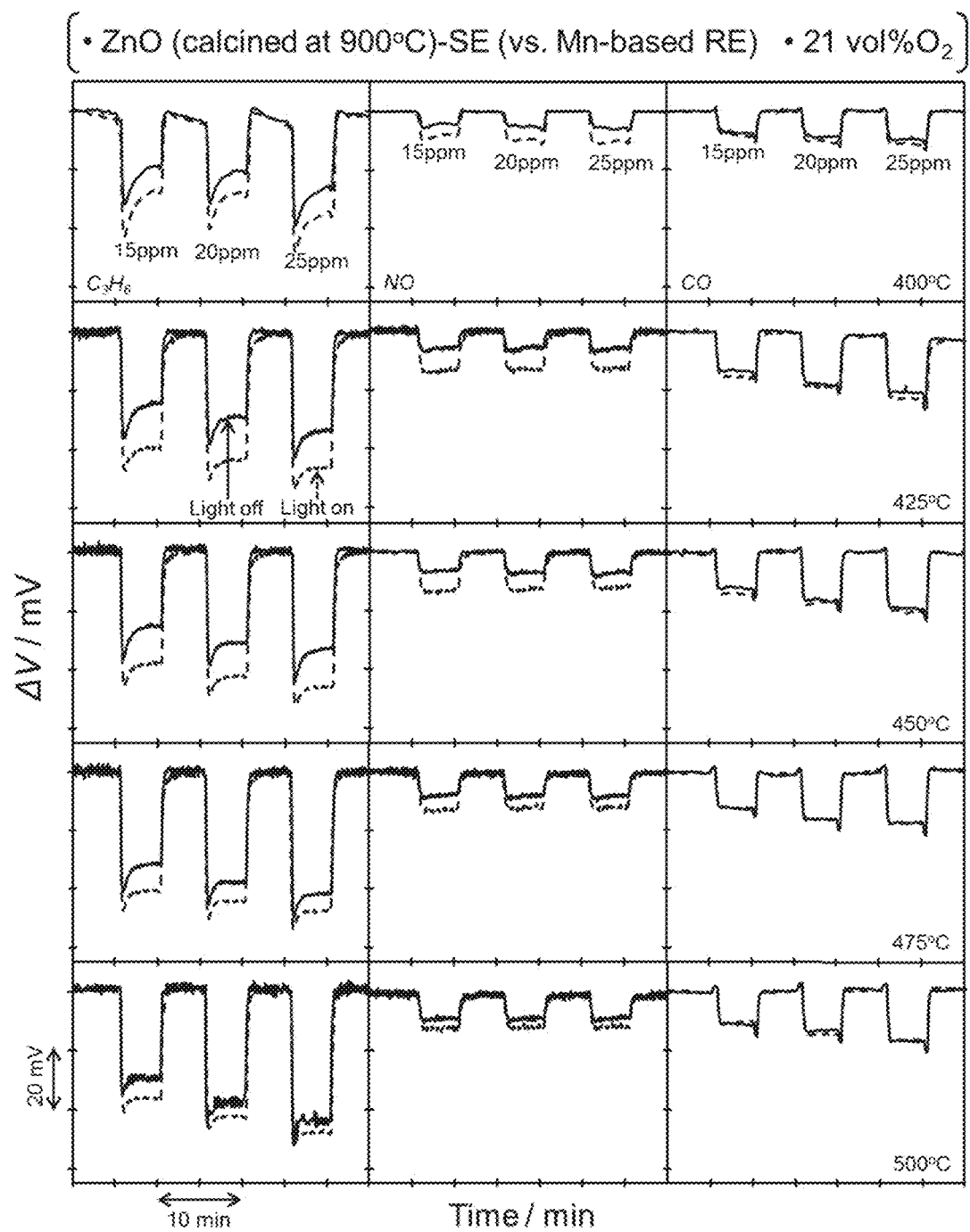
FIG. 3 shows the response transients to $C_3H_6$, NO and CO (in the range of 15-25 ppm) for a sensor part using ZnO-SE (calcined at 900° C.) and Mn-based RE, operated at 400-500° C., with or without illumination. Upon illumination, the sensor part which was operated at 425° C. showed the largest response magnitude to all the examined gases.

FIG. 2 shows the response magnitude in terms of change in voltage ($\Delta V$) to $C_3H_6$ (15 ppm) for a sensor part using zinc oxide-based sensing electrode (ZnO-SE) and Mn-based reference electrode (Mn-RE), operated at 450° C., with (light on) and without illumination (light off). FIG. 3 shows the response transients to $C_3H_6$, NO and CO for a sensor part using ZnO-SE and Mn-based. RE, operated at 400-500° C., with or without illumination. In brevity, followed by calcined at 900° C. and operated at 425° C., the illuminated sensor part (comprised of ZnO-SE) reached its maximum response magnitude to all the examined gases.

Figure 4:
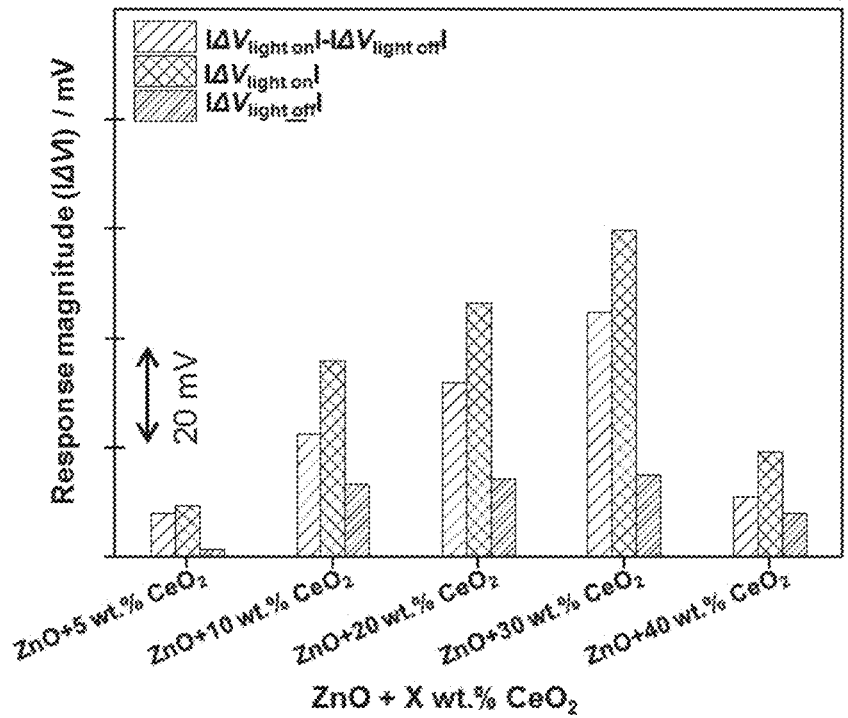
FIG. 4 shows the response magnitude to $C_3H_6$ (15 ppm) for three sensor parts comprised of various binary combinations of ZnO-based composite (ZnO/$Ce_2O_3$) and Mn-based RE, with or without illumination. The amount of additive ($Ce_2O_3$) varied in the range of 5-40 wt. %.
Figure 5:
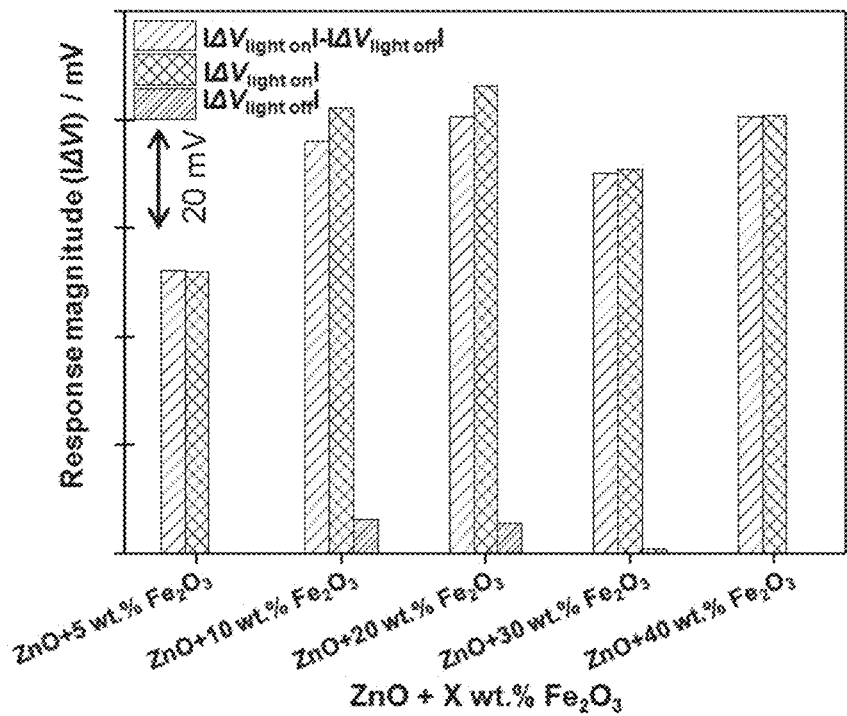
FIG. 5 shows the response magnitude to $C_3H_6$ (15 ppm) for three sensor parts comprised of various binary combinations of ZnO-based composite (ZnO/$Fe_2O_3$) and Mn-based RE, with or without illumination. The amount of additive ($Fe_2O_3$) varied in the range of 5-40 wt. %

Based on these findings, the chemical composition and operational temperatures for the rest of the sensor parts comprised of $ZnO/CeO_2$, $ZnO/Fe_2O_3$ composites SEs were further optimized (shown in FIG. 4 and FIG. 5). It was discovered that the optimum chemical composition for $ZnO/CeO_2$ and $ZnO/Fe_2O_3$ composite electrodes is ZnO+30 wt. % $CeO_2$ and ZnO+20 wt. % $Fe_2O_3$, respectively. Besides, 425° C. was selected as the optimum operational temperature for all the sensor parts.

Figure 6A:
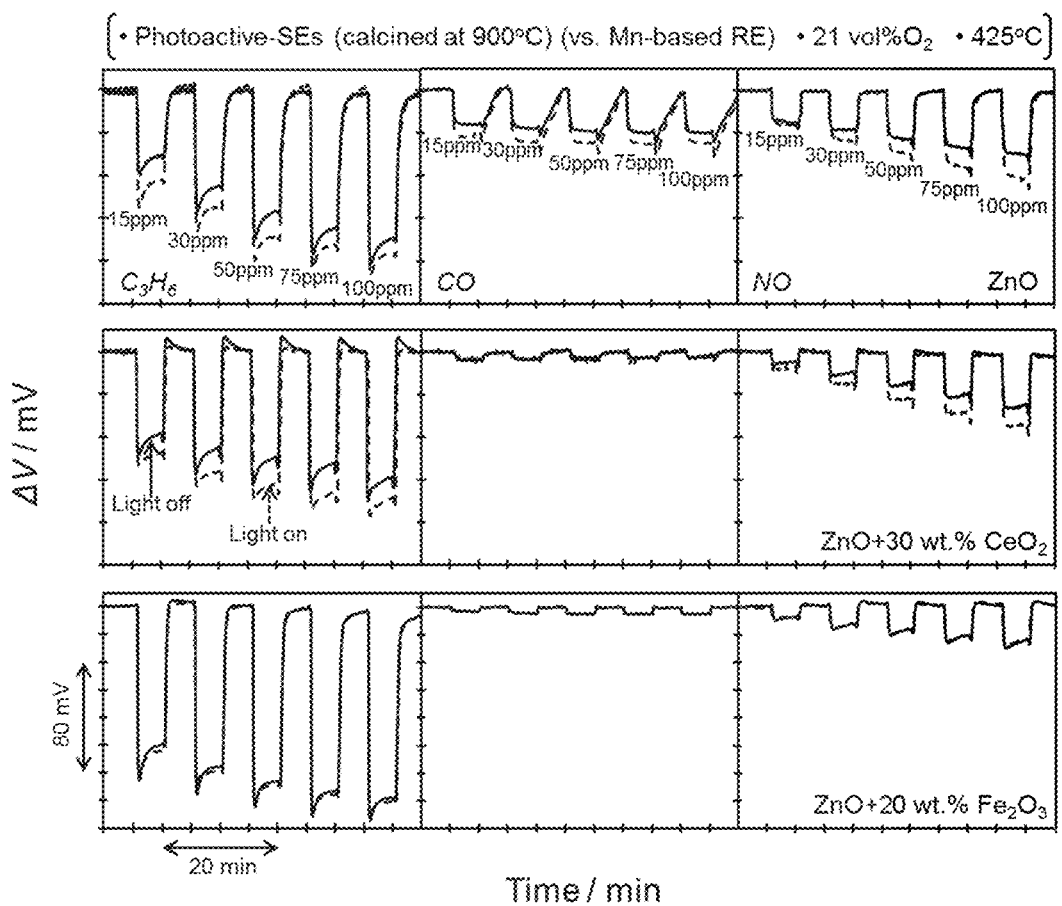
FIGS. 6A and 6B show the sensing behavior towards $C_3H_6$, NO and CO of an electrochemical sensor array comprising three sensor parts (ZnO, ZnO/30% $Ce_2O_3$, ZnO/20% $Fe_2O_3$) and Mn-based RE.
Figure 6B:
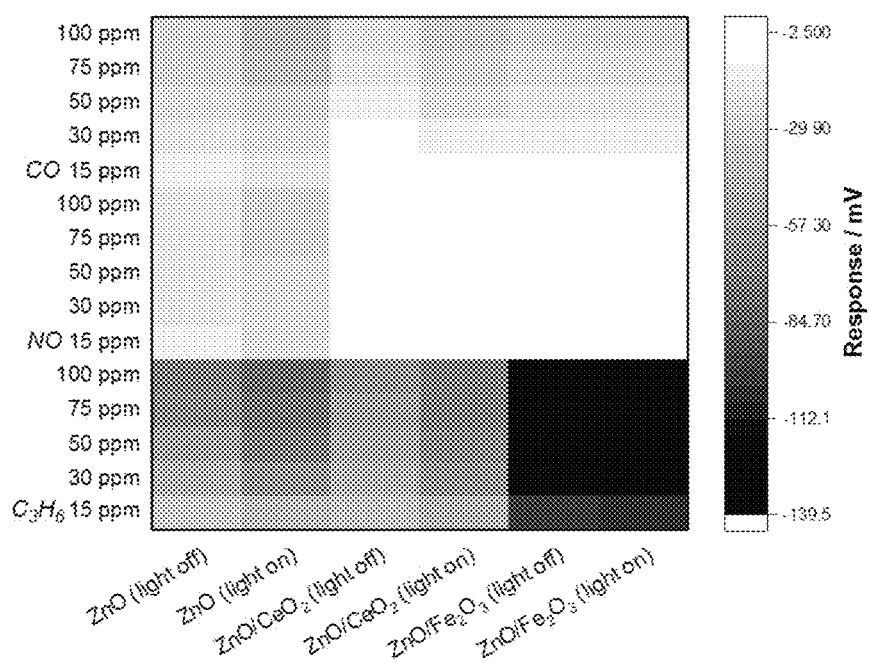
Figure 7A:
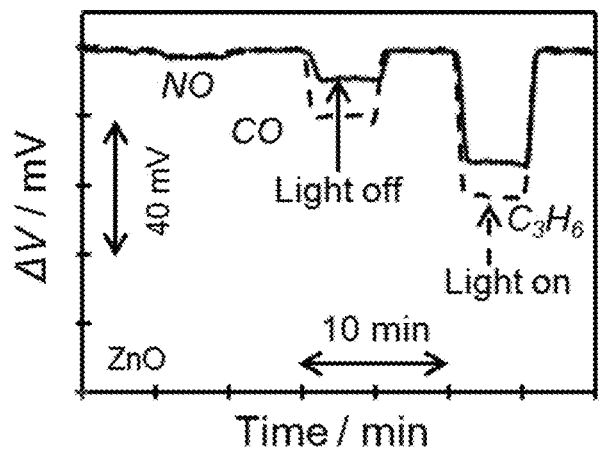
FIGS. 7A-C show the response transients of a sensor array comprising three sensor parts (ZnO, ZnO/30% $Ce_2O_3$, ZnO/20% $Fe_2O_3$) and Mn-based RE, operated with illumination (dotted lines) or without illumination (solid lines), towards 25 ppm of $C_3H_6$, NO and CO.
Figure 7B:
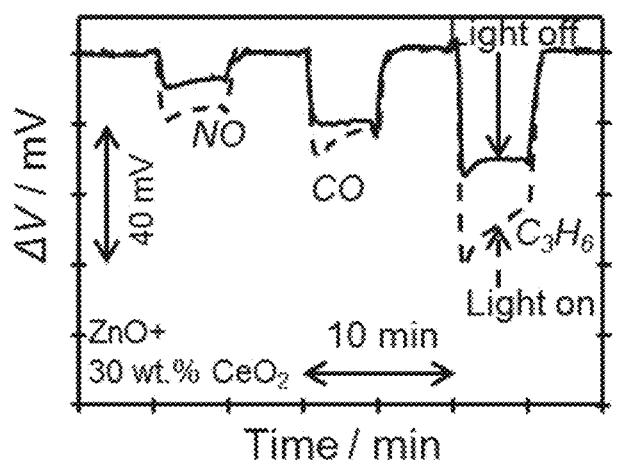
Figure 7C:
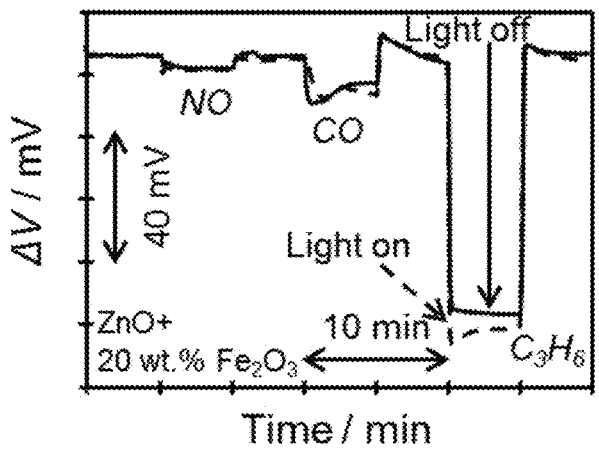
Figure 8C:
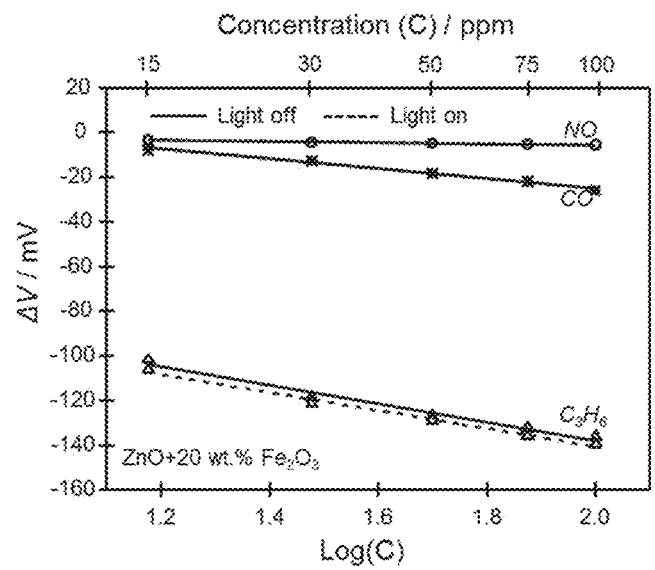

Then, an electrochemical sensor array comprised of these three sensor parts (i.e. sensor part consisting of ZnO-SE, (ZnO+30 wt. % $CeO_2$)-SE or (ZnO+20 wt. % $Fe_2O_3$)-SE was fabricated. FIG. 1 is a photograph of one embodiment of the present sensor array in which all the sensor parts share a Mn-based RE. Its sensing behavior to $C_3H_6$, NO and CO in the range of 15-100 ppm with and without illumination can be seen in FIG. 6A. Interestingly, in comparison with the sensing behavior recorded at light off and light on, the sensor array showed disparate response patterns. In order to give a clearer vision on the impact of illumination, sensing behavior recorded at light off and on were depicted in the form of heat map (FIG. 6B) in which different color represent sensing magnitude to specific gas of a particular sensor part and illumination status. The data indicated that when the sensor array was illuminated, sensing response to the examined gases was selectively enhanced. For instance, the sensor part using ZnO-SE (operated at light on) revealed enhanced sensing response to all the examined gas species, while the enhanced performance for the sensor parts utilizing (ZnO+30 wt. % $CeO_2$)-SE and (ZnO+20 wt. % $Fe_2O_3$)-SE were solely found for the gas species of "$C_3H_6$ and CO" and "$C_3H_6$" respectively. This conclusion can be further confirmed in FIG. 7, FIG. 8 and table 1 which illustrate that illumination significantly improved the sensitivity and detection limit of the sensors toward $C_3H_6$, NO and CO, and the resultant sensor array gave 3 more response patterns when illuminated (FIG. 6).

TABLE 1

Sensing magnitude at 15 ppm, sensitivity and detection limit for the sensor array operated at light off & on, toward $C_3H_6$, NO and CO.

| Sensing materials | Target gas | $-\Delta V$ (at 15 ppm)/mV light off | $-\Delta V$ (at 15 ppm)/mV light on | Sensitivity/ (mV/Dec.) light off | Sensitivity/ (mV/Dec.) light on | Detection limit/ppm light off | Detection limit/ppm light on |
|---|---|---|---|---|---|---|---|
| ZnO | $C_3H_6$ | 30.12 | 43.15 | −43.17 | −47.66 | 3.79 | 1.98 |
|  | NO | 16.11 | 22.42 | −4.22 | −4.97 | 5.75 | 3.17 |
|  | CO | 15.21 | 16.32 | −17.06 | −29.38 | 5.97 | 3.84 |
| ZnO + 30 wt. % $CeO_2$ | $C_3H_6$ | 38.14 | 48.0 | −23.81 | −25.28 | 2.98 | 1.01 |
|  | NO | 2.85 | 2.89 | −1.44 | −1.49 | 14.9 | 14.3 |
|  | CO | 4.94 | 8.16 | −23.48 | −30.03 | 12.1 | 5.37 |
| ZnO + 20 wt. % $Fe_2O_3$ | $C_3H_6$ | 101.79 | 106.14 | −40.50 | −41.69 | 0.857 | 0.751 |
|  | NO | 3.05 | 3.11 | −2.77 | −2.92 | 14.7 | 14.0 |
|  | CO | 12.64 | 12.64 | −22.11 | −22.15 | 4.57 | 4.57 |

Figure 9A:
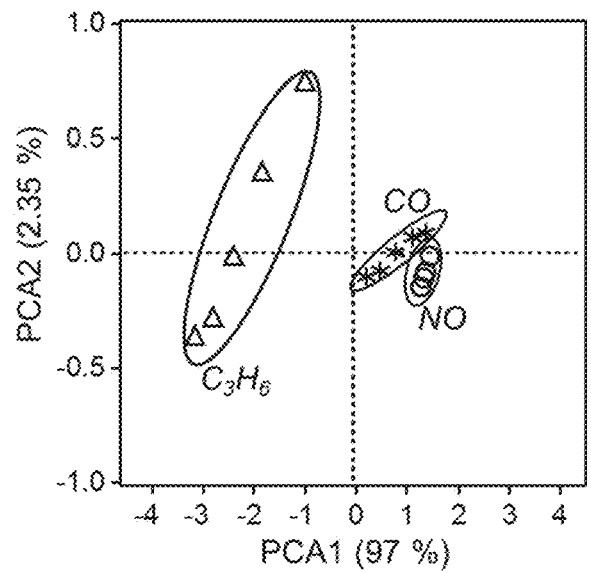
FIGS. 9A and 9B show the principal component analysis (PCA) transformation of the data set for a light-regulated electrochemical sensor array. PCA transformation generated by processing three response patterns derived from a sensor array comprised of three sensor parts which was solely operated at light off (FIG. 9A); or six disparate response patterns derived from a sensor array comprised of 3 sensor parts which was operated at light off and light on (FIG. 9B). PCA1 and PCA2 represent different quadrant, while the value of percentage in PCA1 and PCA2 respectively represent the amount of data sets in quadrant 1 (PCA1) and quadrant 2 (PCA2).
Figure 9B:
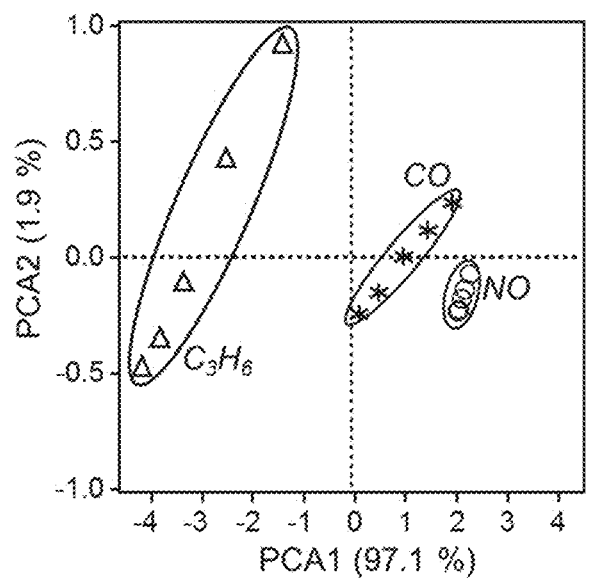

As observed from FIG. 6, since three more response patterns were obtained by exposing the sensor array to illumination, it is expected that a sensor array which operates with and without illumination will generate a better discrimination of the examined gases as compared to sensors which operates solely without illumination or solely with illumination. To confirm this, principal component analysis (PCA) transformation was depicted via processing all the six response patterns (i.e. three obtained at light off, three obtained at light on) with PCA algorithm. Since one sensor part alone is usually not selective enough to sufficiently differentiate one gas molecule from another, the present invention adopts the PCA transformation to process all the response patterns obtained from all the sensor parts in the sensor array so as to sufficient identify a particular species of gas molecules. Since different gas molecules locate at different position of the PCA translation (such as CO and $C_3H_6$ in FIG. 9A-9B), the present invention can classify and identify different species of gas molecules using a plurality of sensor parts and further with the aid of illumination.

In one embodiment, a feature vector of 15×6 (row× column) consisting of response patterns to these hazardous gases in the range of 15-100 ppm was created as the input to PCA. The same colored symbol within the PCA transformation corresponds to a specific gas and a large spatial distance between these symbols suggests a desirable discrimination feature given by the sensor array. The PCA transformation shown in FIG. 9A derives from the sensor array operated without illumination (i.e. by solely input three response patterns). Obvious overlap was observed for PCA transformation of CO and NO, suggesting serious mutual interference will be resulted if the sensor array (operated at light off) is used for sensing a gas mixture of CO and NO. In contrast, satisfactory discrimination feature (FIG. 9B) is generated by inputting the six response patterns derived from the sensor array operated with and without illumination. In other words, the results indicated that, with the aids of illumination all the examined gases can be artificially classified with high selectivity. These results indicate that light-regulated electrochemical reaction can provide an efficient approach for designing next generation low power and compact smart sensing devices with enhanced sensitivity and detection limit, and particularly with promoted discrimination capability.

In one embodiment, response pattern obtained is analyzed by a pattern recognition algorithm such as principal component analysis (PCA). In one embodiment, response pattern obtained is analyzed by pattern recognition algorithm such as multi-layer perception (MLP), generalized regression neural network (GRNN), fuzzy inference systems (HS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

B) Sensing Behavior of the Light-Regulated Electrochemical Sensor Array to VOCs (Toluene, Nonane, Ethylbenzene n-Hexane Benzene, Acetone)

Volatile organic compounds (VOCs), such as toluene, nonane, ethylbenzene, and n-hexane that exhaled from breath samples are useful biomarkers for early detection of some diseases. Therefore, smart sensing devices that can monitor these VOCs in the range of hundreds of ppb (parts per to several ppm (parts per million) is particularly important from the perspective of human healthcare. However, one of the challenging issues in detecting VOCs at low concentration is the subtle response signal generated by the sensing devices which results in inadequate detection limit. Apart from detecting limit, distinguishing capability is also crucial such that the device can distinctively detect a particular type of VOCs when facing a mixture of VOCs.

In the above section, it was found that sensing ability, namely the sensitivity, detection limit and selectivity of electrochemical gas sensors can be significantly improved by illumination. This section further investigates the distinguishing capability towards a larger number of gases (which are VOCs) of the sensors. It is expected that a sensor array comprising a limited number of sensor parts can generate more response patterns when used in combination and treated by illumination and is therefore able to synergistically classify and identify more number of target gas molecules (e.g. a sensor array composed of three sensor parts can identify six kinds of target gases). To verify this presumption, the present invention fabricated an YSZ-based electrochemical gas sensor array comprised of several ZnO/$In_2O_3$ composites (as the sensing materials) and Mn-based reference electrode.

Figure 10A:
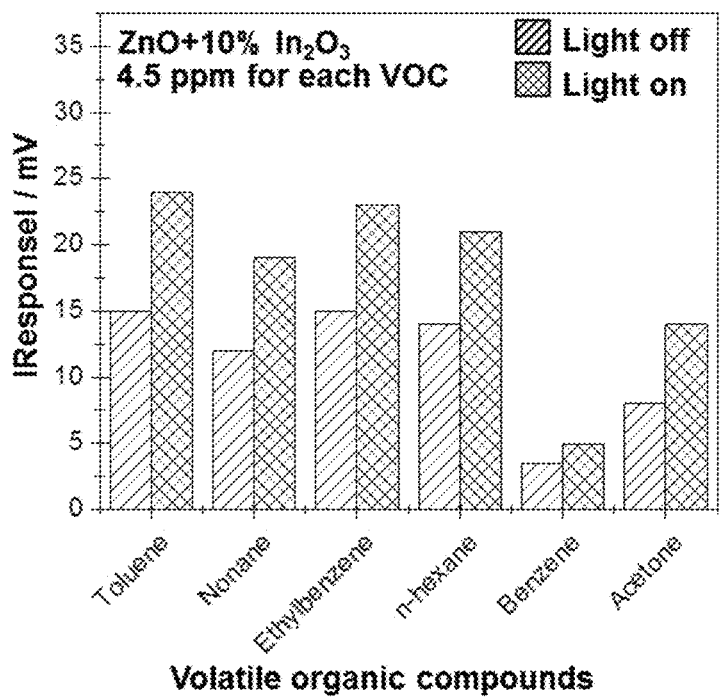
Figure 10B:
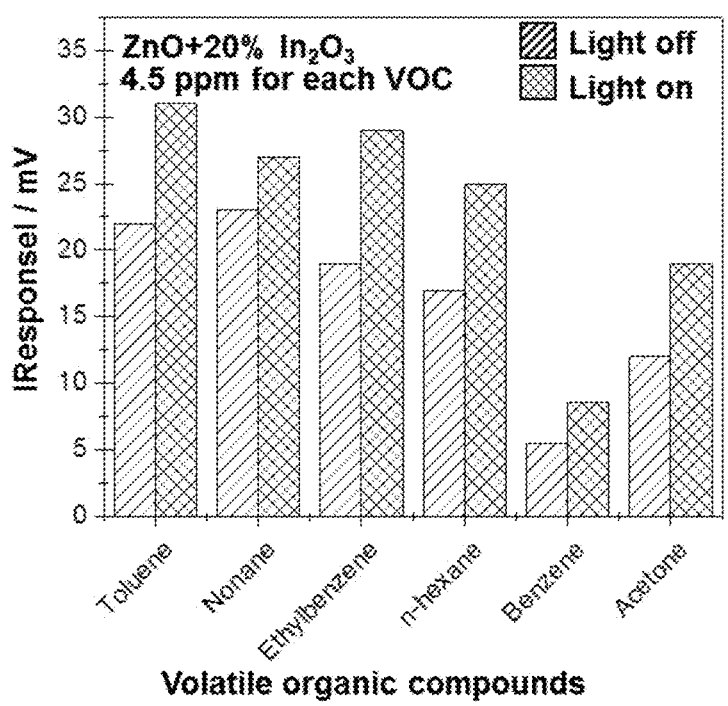
Figure 10C:
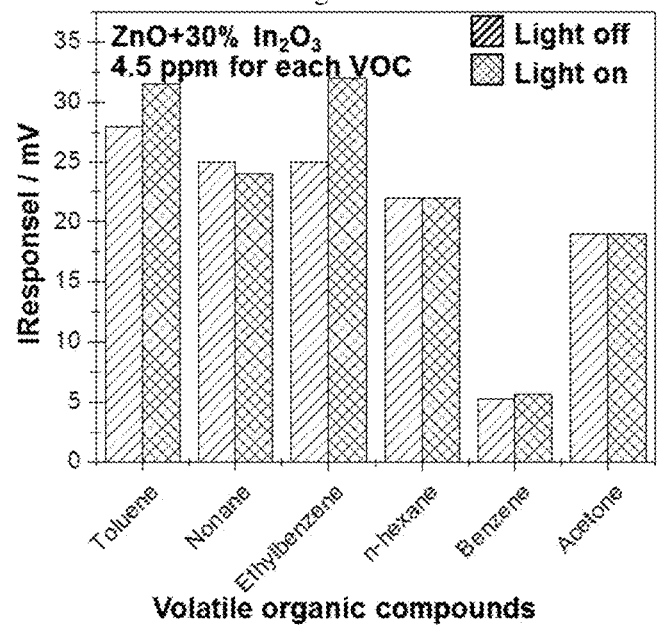

To simplify the fabrication technique and essentially modify the distinguish capability of the electrochemical sensor, a YSZ-based sensor array comprised of zinc oxide/Indium(III) oxide (ZnO/$In_2O_3$) composite sensing electrodes (SEs) and a Mn-based reference electrode (RE) was fabricated and its ability in distinguishing six selected VOCs was systemically studied. Initially, sensing behavior of the zirconia-based sensors comprised of (ZnO+10-30% In$_2$O$_3$)-SEs and Mn-based RE was evaluated (shown in FIG. 10A). It was found that the addition of In$_2$O$_3$ into ZnO significantly modified the sensing behavior, resulting in disparate response patterns for sensors using various ZnO/In$_2$O$_3$-SEs. Particularly, response signals to all the examined. VOCs increased as the amount of In$_2$O$_3$ in the zinc-based composite increased. The maximum response signal observed was from the sensor consisting of (ZnO+30% In$_2$O$_3$)-SE. These result suggested that ZnO/In$_2$O$_3$ composite is favorable for generating high response signal. However, further increment of In$_2$O$_3$ up to 40% in the composite declined the response magnitude which maybe attribute to the high gas-phase reaction, the response signal to all the examined VOCs decreased 20% when compared that of the sensor comprised of (ZnO+30% In$_2$O$_3$)-SE (vs. Mn-based RE) (data not provided). In order to further enhance the response signal and to investigate the impact of illumination, response behavior of these sensors utilizing various types of ZnO/In$_2$O$_3$-SEs was recorded with illumination. As shown in FIGS. 10A-10C, illumination gave a relatively large impact on the sensing performance of the sensors consisting of (ZnO+10-30% In$_2$O$_3$)-SEs. On average, the enhancement in the response magnitude to most of the examined VOCs reached 20% for the sensors composed of (ZnO+10-30% In$_2$O$_3$)-SEs upon illumination. Selectively enhanced response signal was also observed for these illuminated sensors. Typically, apparent increment in the sensing signal of all the examined VOCs can be seen for sensor consisting of (ZnO+10% In$_2$O$_3$)-SE (FIG. 10A), while for sensor using (ZnO+20% In$_2$O$_3$)-SE (FIG. 10B), a relatively large enhancement was observed for response signal of some VOCs (toluene, ethylbenzene, n-hexane and acetone). On the contrary, the sensor comprised of (ZnO+30% In$_2$O$_3$)-SE (FIG. 10C) solely demonstrated obvious improvement in detecting two VOCs (toluene and ethylbenzene).

Figure 10D:
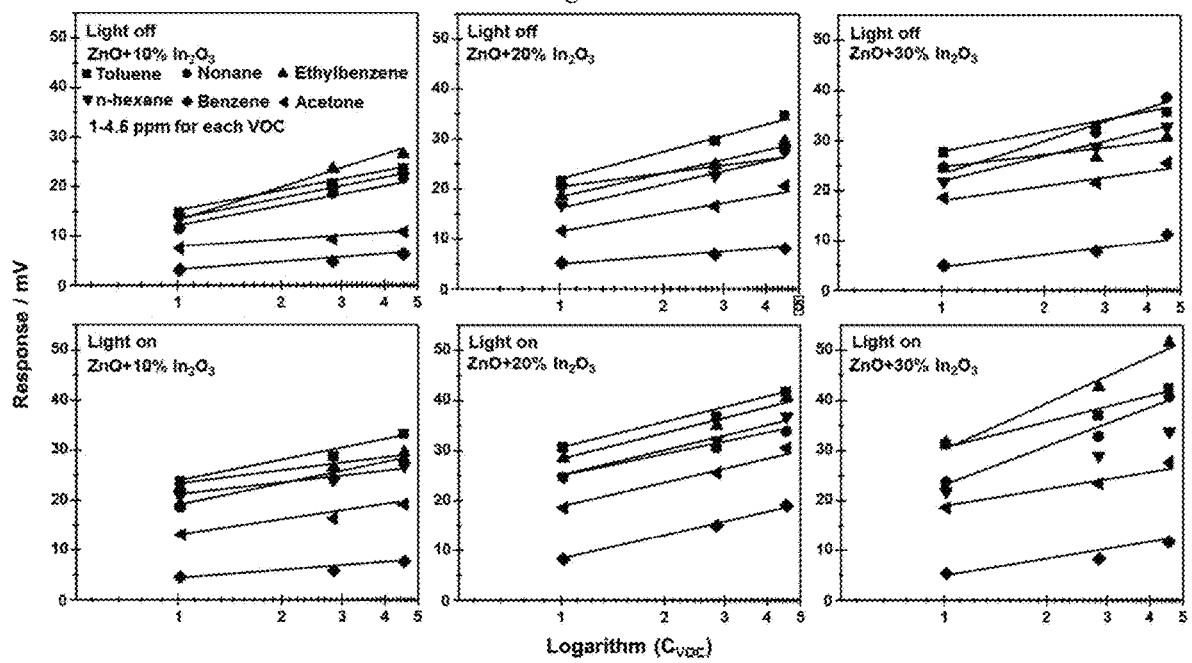

To confirm the conclusion, dependence of the response signal on the concentration of examined VOCs was examined and shown in FIG. 10D. Linear relationship between the response signal and the logarithm of gas concentration was observed for these sensors regardless of the SEs used. Moreover, the results illustrate that illumination significantly affected the sensing performance of the sensor and in particular response signal of the examined VOCs was selectively increased for the sensor consisting of (ZnO+30% In$_2$O$_3$)-SE. Table 2 summarizes the difference in the detection limit for the sensors utilizing (ZnO+(10-30)% In$_2$O$_3$)-SEs and Mn-based RE, operated with light off or light on in relation to these selected VOCs.

In short, the detection limit for the examined VOCs can be further improved to a desirable value with the assistance of illumination. The date presented in this invention proved that illumination is beneficial to enhancing the sensing performance of the YSZ-based sensors consisting of photoactive ZnO/In$_2$O$_3$-SEs. Since the addition of 10-30% In$_2$O$_3$ into ZnO resulted in significant enhancements in the response signal upon illumination treatment, an YSZ-based electrochemical sensor array comprised of these sensing materials (as sensing electrodes) was fabricated It is expected that more plentiful response patterns will be given by this sensor array when been operated at light off and on.

TABLE 2

Sensing magnitude at 1 ppm of VOCs and detection limit for the sensor consisting of (ZnO + (20-40)% In$_2$O$_3$) composite SEs, operated at 425° C. with light off or on.

| Materials | VOCs | −ΔV (at 1 ppm)/mV | | Detection limit/ppm | |
|---|---|---|---|---|---|
| | | Light off | Light on | Light off | Light on |
| ZnO + 10% In$_2$O$_3$ | Toluene | 15.1 | 24.6 | 0.669 | 0.330 |
| | Nonane | 12.4 | 19.5 | 0.729 | 0.507 |
| | Ethylbenzene | 15.3 | 23.0 | 0.607 | 0.548 |
| | n-hexane | 14.7 | 21.1 | 0.639 | 0.493 |
| | Benzene | 3.52 | 4.99 | 0.754 | 0.591 |
| | Acetone | 8.43 | 14.7 | 0.792 | 0.446 |
| ZnO + 20% In$_2$O$_3$ | Toluene | 22.2 | 31.7 | 0.481 | 0.092 |
| | Nonane | 21.4 | 25.3 | 0.383 | 0.099 |
| | Ethylbenzene | 19.3 | 29.7 | 0.459 | 0.087 |
| | n-hexane | 17.5 | 25.9 | 0.504 | 0.104 |
| | Benzene | 5.56 | 8.62 | 0.317 | 0.109 |
| | Acetone | 12.0 | 19.4 | 0.671 | 0.096 |
| ZnO + 30% In$_2$O$_3$ | Toluene | 28.3 | 31.5 | 0.318 | 0.117 |
| | Nonane | 24.7 | 25.1 | 0.278 | 0.263 |
| | Ethylbenzene | 25.6 | 32.5 | 0.111 | 0.042 |
| | n-hexane | 22.1 | 22.2 | 0.301 | 0.142 |
| | Benzene | 5.32 | 5.76 | 0.416 | 0.184 |
| | Acetone | 19.1 | 19.3 | 0.328 | 0.299 |

Figure 11:
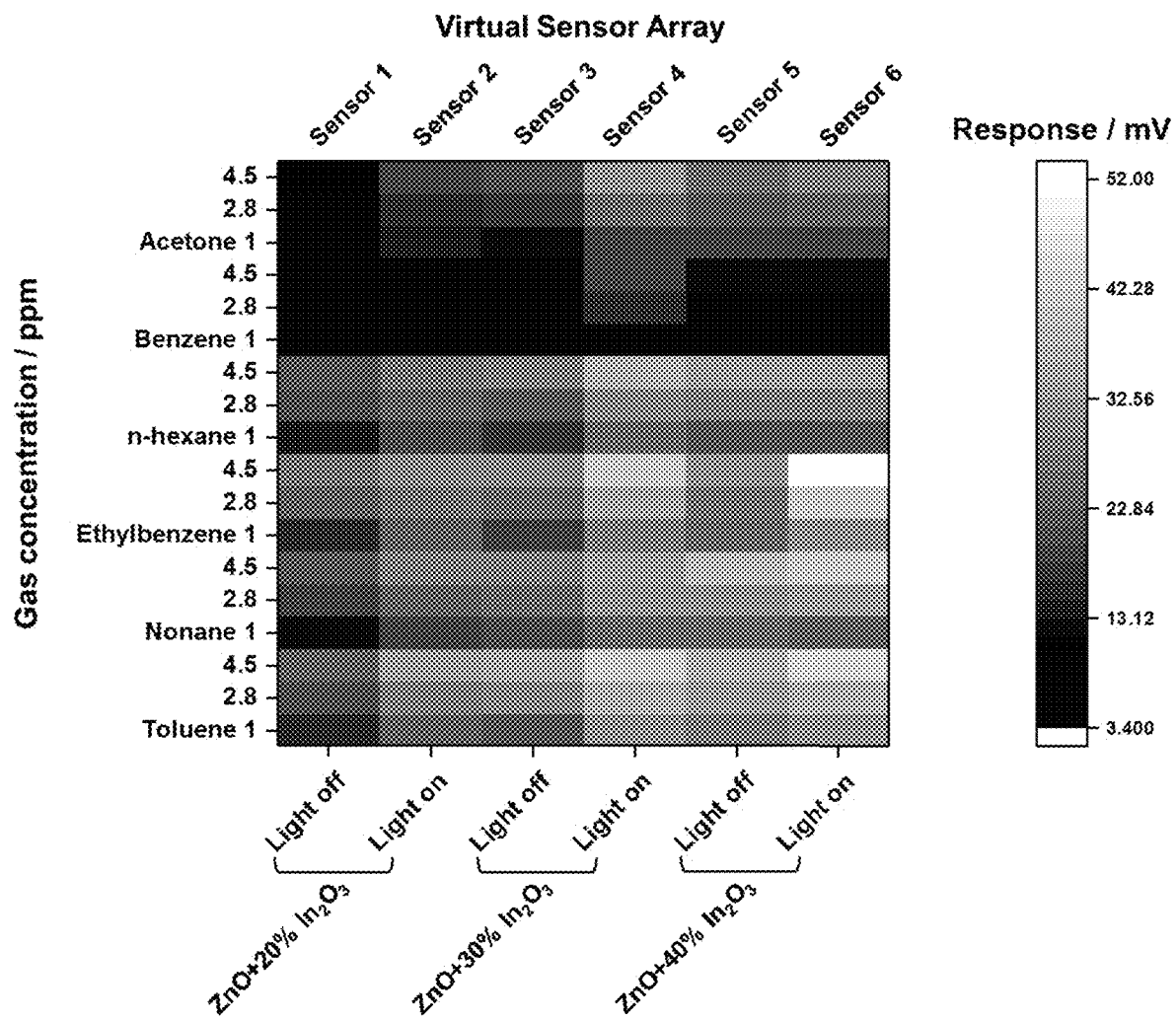
FIG. 11 shows the response patterns for the electrochemical sensor array comprised of (ZnO+(10-30)%)-SEs and Mn-based RE, depicted in the form of a heat map.

To give a clearer vision on the impact of illumination and the amount of In$_2$O$_3$ on the sensing behavior, sensing behavior of the sensor array that recorded at light off and on was depicted in the form of a heat map in which different colors represent the corresponding sensing magnitude to a specific VOC (FIG. 11). As expected, when operated at light off and light on, completely different response patterns were generated. In sum, by a simple exposure to illumination, six response patterns (i.e., three obtained at light off, three obtained at light on) are obtained although the sensor array only comprised of three types of ZnO/In$_2$O$_3$ sensing materials. If considering each response pattern is given by a single sensor, the sensing characteristics demonstrated by the sensor array (operated at light off and on) is equivalent to that of a virtual sensor array consisting of six virtual sensors (as shown in FIG. 11). As observed in FIG. 11, since disparate response patterns were generated at light on as compared to operation at light off, it is expected that a sensor array which operates with and without illumination will have a better classification feature as compared to sensor array which operates solely without illumination or solely with illumination.

Figure 12A:
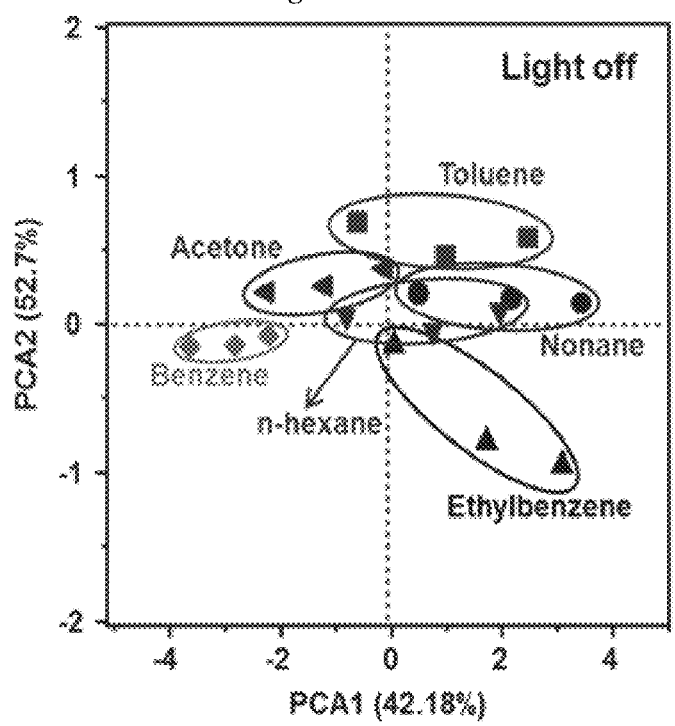
Figure 12B:
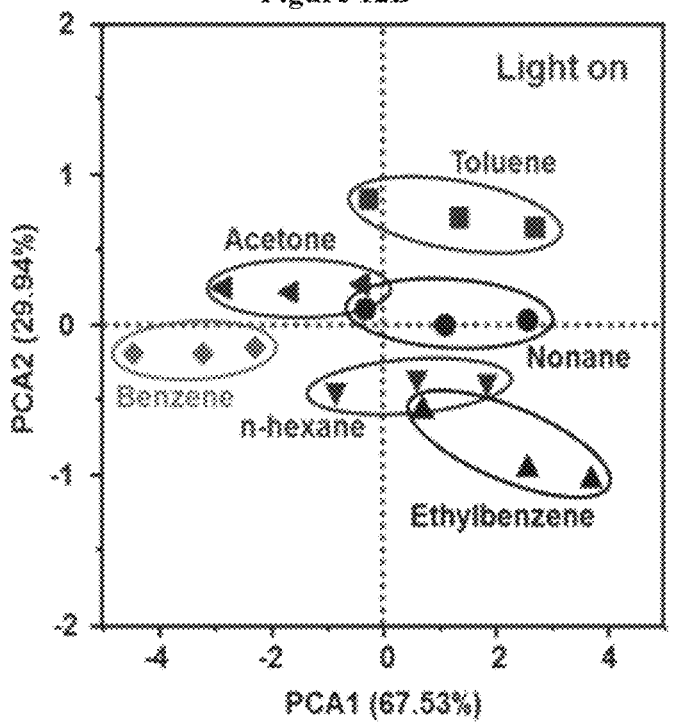

FIG. 12 shows the plot of PCA transformation as a result of processing the obtained six response patterns with PCA algorithm. In brevity, a feature vector of 18×6 (row×column) consisting of response patterns to these indoor harmful VOCs in the range of 1-4.5 ppm was created as the input to PCA. FIG. 12A and FIG. 12B show the PCA transformation derived from the sensor array solely operated at light off or light on. Apparent overlap was found for vast majority of the examined VOCs, indicating that serious mutual interference will be resulted when the sensor array operated at light off or light on is used for sensing a mixture of these VOCs. In contrast, desirable classification feature was obtained by processing the six response patterns derived from the sensor array operated at light off and on (shown in FIG. 12C). These result indicated that all the examined VOCs can be differentiated and the light-regulated electrochemical reaction can significantly modify the distinguishing capability of sensors. In conclusion, after exposure to illumination the sensor array consisting of limited photoactive sensing materials (e.g.

three types of sensor parts) can synergistically identify more number of gases (e.g. six kinds of VOCs).

Detection and Diagnosis of Disease or Health Status Using the Present Sensor Arrays In one embodiment, the present invention provides methods and devices for detecting and distinguishing various types of gas molecules or volatile organic compounds (VOCs).

In one embodiment, the present invention provides methods and devices for diagnosing a disease in a subject or a health status of a subject through the detection of VOCs indicative of the disease or health status in question from breath of the subject.

In one embodiment, the methods and devices for diagnosis comprises any one of light-regulated electrochemical sensor arrays described herein.

In one embodiment, the light-regulated electrochemical sensor array to be used comprises a plurality of sensing electrodes. In one embodiment, the minimum number of the sensing electrodes in the sensor array is N/2, where N is the number of target VOCs to be identified.

In one embodiment, VOCs to be detected by the present invention for the purpose of diagnosis are VOCs that are known to be indicative of the presence or stage of a particular diseases.

In one embodiment, diseases to be detected or diagnosed using the present invention include but not limited to cancers, infectious diseases, endocrine diseases, metabolic diseases, genetic diseases, diseases of the nervous system and sense organs, diseases of the circulatory system, diseases of the respiratory system, diseases of the digestive system, diseases of the genitourinary system, diseases of the skin and subcutaneous tissue, diseases of the musculoskeletal system and connective tissue, and congenital anomalies.

In one embodiment, the subject is a human. In one embodiment, the subject is an animal.

In one embodiment, the present invention is used for the detection and diagnosis of colorectal cancer and its stage. In one embodiment, VOCs to be detected by the present invention for the purpose of detecting or diagnosing colorectal cancer are VOCs that are known to be indicative of the existence of colorectal cancer or the stage of colorectal cancer. In one embodiment, VOCs to be detected by the present invention for the purpose of detecting or diagnosing colorectal cancer are VOCs that are reported in Di Lena M et al., the entire contents of which are incorporated herein by reference into this application.

In one embodiment, the present invention is used for the detection and diagnosis of heart failure and its sub types. In one embodiment, VOCs to be detected by the present invention for the purpose of detecting or diagnosing heart failure are VOCs that are known to be indicative of the existence of heart failure or the different types of heart failure. In one embodiment, VOCs to be detected by the present invention for the purpose of detecting or diagnosing heart failure are VOCs that are reported in Fabiana G et al., the entire contents of which are incorporated herein by reference into this application.

Detection and Analysis of VOCs Related to Lung Cancer

In one embodiment, the present invention provides methods and devices for detecting the existence of lung cancer in a subject through the detection of VOCs indicative of the existence of lung cancer from breath of the subject.

In one embodiment, the present invention provides methods and devices for diagnosing lung cancer or determining the stage of lung cancer in a subject through the detection of VOCs indicative of the existence or progression of lung cancer from breath of the subject.

In one embodiment, the present invention provides methods and devices for identifying the subtype of lung cancer in a subject having lung cancer through the detection of VOCs indicative of the presence of the subtype of lung cancer in question from breath of the subject.

In one embodiment, the methods and devices tier diagnosis of lung cancer comprises any one of light-regulated electrochemical sensor arrays described herein.

In one embodiment, VOCs to be detected by the present invention for the purpose of detecting or diagnosing lung cancer are VOCs that are known to be indicative of the existence of lung cancer, the subtype of lung cancer or the stage of lung cancer. In one embodiment, VOCs to be detected by the present invention for the purpose of detecting or diagnosing lung cancer are VOCs that are reported in Poli et al. (19) or Peng et al. (20), the entire contents of which are incorporated herein by reference into this application.

In one embodiment, VOCs to be detected by the present invention for the purpose of detecting or diagnosing lung cancer are VOCs that are newly identified. Example 3 describes procedures for identifying VOCs relevant to lung cancer by studying the VOCs profile of healthy subjects and lung cancer patients.

Characterization of Signature Volatile Profiles Via Specified Diagnostic Sensing Materials In one embodiment, the present invention provides sensor arrays that are sensitive to VOCs indicative of lung cancer. In one embodiment, the present invention provides a sensor array that is capable of detecting lung cancer-related VOCs in a highly sensitive and selective manner, therefore can be applied to perform an accurate and efficient diagnosis of lung cancer by analyzing breath sample of a subject.

Example 4 describes procedures for preparing lung cancer-specific sensor arrays and validation of these arrays in their ability in detecting lung cancer-specific VOCs.

In one embodiment, the present sensor array for lung cancer diagnosis comprises a plurality of light-regulated, gas sensing sensors that are sensitive to lung cancer-specific VOCs, where these gas sensing sensors can detect lung cancer-specific VOCs in a more sensitive and selective manner as compare to detection using one or some of these gas sensing sensors. In one embodiment, the present sensor array for lung cancer diagnosis comprises 6-8 light-regulated, gas sensing sensors.

In one embodiment, the present sensor array for lung cancer diagnosis comprises one or more of light-regulated, gas sensing sensors described herein.

In one embodiment, the photoactive sensing electrodes are made of photoactive metal oxides such as zinc oxide or zinc oxide-based materials (e.g. $ZnO/CeO_2$, $ZnO/In_2O_3$, $ZnO/Bi_2O_3$), and titanium-based materials as well as photoactive perovskite. In one embodiment, the photoactive sensing electrodes are made of zinc oxide-based materials, titanium-based materials or photoactive perovskite doped with p-type metal oxides (e.g. NiO, CuO, $Cr_2O_3$).

In one embodiment, the reference electrode is comprised of manganese tetroxide ($Mn_3O_4$) or platinum (Pt).

Design of a Tailor-Made Artificially Intelligent Sensor Array for Lung Cancer Diagnosis and Clinical Testing In one embodiment, the present invention provides a device for detecting or diagnosing lung cancer or its subtypes.

In one embodiment, the present invention provides a device for detecting or diagnosing lung cancer which is operated with an artificially intelligent algorithm.

In one embodiment, the present device for detecting or diagnosing lung cancer comprises one or more of the following: a breath collector comprising one or more pre-concentrators for concentrating breath analytes to be detected and a dehumidifying unit for removing water vapor from the breath sample, a pump system for sucking the breath sample exhaled from human breath to the device, a gas chamber for storing the breath sample and exposing the sensor array to breath sample, one or more sensor arrays for sensing VOCs derives from the breath sample, a light source such as a light-emitting diode (LED) light to supply illumination to the sensor array, a detection unit for measuring electric signals as a result of oxidation or reduction of the VOCs at the sensor array, an analyzer for analyzing the response pattern obtained from the breath sample, a data communication chip for wireless communication between the device and a host computer/database, a display screen (e.g. a LED display), a control system for controlling the operation of the device, comprising a single chip microcomputer for managing the device and relevant circuits (including a controlling circuitry for operating the pump and maintaining the regular work of sensor array, a processing circuitry for processing the signals from the sensory arrays).

In one embodiment, the sensor array is embedded within the gas chamber so that breath samples are exposed to the sensor array after they pass from the breath collector to the gas chamber, and the sensor array detects VOCs in the breath sample subsequently.

In one embodiment, the present device comprises a plurality of operating sensors and regulators for measuring and regulating various operating parameters such as temperature, pressure, humidity and air velocity respectively. In one embodiment, the operating sensors send feedback signals to the control system and the regulators maintain or adjust their respective operating parameters in response. In one embodiment, the present device controls and monitors one or more of the following: velocity of air within the device, the exposure angle to the sensor array, pressure and temperature in various compartments of the device. As such, operation of the device from collection of breath sample to detection of target VOCs can be tightly regulated and monitored.

In one embodiment, the pre-concentrator comprises a solid phase microextraction (SPME) fiber which is coated with a liquid (polymer), a solid (sorbent) or a combination thereof. In one embodiment, the fiber is coated with a liquid and extracts the gas analytes from a sample by absorption. In one embodiment, the fiber is coated with a solid and extracts the gas analytes from a sample by adsorption. In one embodiment, the fiber is subject to desorption at a high temperature such as 150° C. in which the gas analytes collected are desorbed and further analyzed by the instant device.

In one embodiment, the pre-concentrator comprises a sorbent tube which is made of various types of solid adsorbed materials such as activated charcoal, silica gel and organic porous polymers (e.g. Tenax and Amberlite XAD resins). In one embodiment, gas analytes adsorbed on the sorbent tube are released by heating at a high temperature such as 150° C. and further analyzed by the instant device.

In one embodiment, the pre-concentrator comprises a cryogenic condensate such as a chlorofluorocarbon (CFC) and liquid nitrogen for condensing the gas analytes and concentrating the gas analytes as a result.

In one embodiment, the dehumidifying unit comprises a material that remove water vapour from a gas sample, including but not limited to silica gel, activated carbon, desiccant or equivalent.

In one embodiment, the device is configured to directly collect air sample from a subject and give diagnostic results within a few minutes.

Example 5 describes procedures for verifying the present device comprising lung cancer specific sensor array using clinical samples and describes one embodiment of the configuration of the present device for lung cancer diagnosis.

In one embodiment, the present invention provides a device or system for detecting gas molecules or VOCs, the device or system comprises some or all of the components of the device for diagnosing lung cancer described herein and is applicable to breath samples and any gas samples containing the target gas molecules or VOCs.

In one embodiment, the following are expected from the present invention:
1) An informative database related to the lung cancer VOCs for Hong Kong locals. The database is expected to include the detail qualitative and quantitative information on VOCs profile for lung cancer and even sub-types of lung cancer.
2) A device comprising the described sensor array for early diagnosing lung cancer via breath sample. The sensor array is expected to be comprised of 6-8 sensors. Each sensor is expected to consist of different photoactive ZnO-based material. The accuracy of prototype for diagnosing lung cancer is expected to be 80-85%, with response time less than 5 min and 8-12 months life time (30 usage count/month). The device does not require much operating power and complex instrumentation, thereby making diagnosis more affordable and simpler.

Expected Significance of the Present Invention

To date, many kinds of portable gas sensors have been proposed for the breath sample analysis which includes but not limited to: semiconductor sensors, quartz crystal microbalance (QCM) sensors, surface acoustic wave (SAW) sensors and electrochemical sensors. Among them, electrochemical sensors demonstrate its merits in high selectivity and reliable performance in harsh condition as well as desirable long-term stability. However, inadequate sensitivity and detection limit restrain the practicability of adopting the electrochemical sensors to analyze breath sample. The present invention have shown that illumination significantly enhanced the response magnitude, sensitivity and detection limit of sensors. Furthermore, the present invention discovered that illumination can significantly enhance selectivity of the sensors. It is confirmed that the ability to distinguish different types of gases of the present light-regulated electrochemical sensor array comprising a plurality of sensors can be essentially enhanced by the illumination. As shown in FIG. 12 of the patent, a sensor array that is composed of 3 sensor parts could not distinguish six kinds of VOCs when the array was solely operated at light off (without illumination) or light on (with illumination). On the contrary, acceptable classification features to the examined six kinds of VOCs were observed by operating the sensor array at light off and light on. In conclusion, these results confirm that methods provided by this invention can significantly enhance the response magnitude, sensitivity and detection limit as well as the selectivity of light-regulated sensor array.

Compared with traditional strategy (i.e., mainly relied on materials exploration using known and well-designed sensing materials), the method described herein provides more efficient ways to enhance the sensing ability of the electrochemical gas sensors. Particularly, the present invention proved that the present light-regulated electrochemical sensor array which is composed of limited number of sensors (e.g. three sensor parts) can successfully identify more number of target gas (e.g. six kinds of VOCs). This implies that the number of sensor parts in the sensor array can be further reduced while keeping a high performance.

Compared with the most semiconductor gas sensors available at the time of this invention, electrochemical gas sensors demonstrate relatively high selectivity and desirable long-term stability for VOCs sensing in high humidity conditions. Meanwhile, having improved gas sensing abilities such as response magnitude, sensitivity, detection limit (down to ppb level) and selectivity and the ability to detect more number of VOCs with a limited number of sensor parts, the present electrochemical sensor array can be utilized in detecting multiple VOCs exhaled from human breath for clinical purposes.

Conclusively, the present invention provides a new type of electrochemical sensors with desirable performance that is suitable for various clinical applications involving the detection or analysis of VOCs. The promising results provided herein indicate a brighter future for progressively smarter monitoring of human body conditions, such as required in clinic diagnosis.

In one embodiment, the present invention provides a method for detecting a disease in a subject, the method comprises:
 a) exposing a sensor array to a test exhaled breath sample obtained from the subject, the sensor array comprises a plurality of sensing electrodes and a reference electrode;
 b) measuring a plurality of electric signals from the sensor array indicating the presence or concentration of a plurality of volatile organic compounds (VOCs); and
 c) analyzing a response pattern obtained from the plurality of electric signals using a pattern recognition algorithm by comparing it with a response pattern obtained from one or more healthy subject, thereby detecting the disease.

In one embodiment of the method, the VOCs are indicative of the existence or stage of the disease.

In one embodiment of the method, the sensor array is a light-regulated electrochemical sensor.

In one embodiment of the method, each of the VOCs either undergoes an oxidation or reduction when it contacts the sensing electrode, thereby resulting in a flow of electrons between the sensing electrode and reference electrode and generating electric signals.

In one embodiment of the method, each of the sensing electrodes comprises one or more of a photoactive metal oxide and a photoactive metal oxide-based material.

In one embodiment of the method, the photoactive metal oxide is zinc oxide or titanium oxide.

In one embodiment of the method, the photoactive metal oxide-based material is zinc oxide/cerium(IV) oxide ($ZnO/CeO_2$), iron(III) oxide ($Fe_2O_3$), zinc oxide/indium(III) oxide ($ZnO/In_2O_3$), zinc oxide/bismuth(III) oxide ($ZnO/Bi_2O_3$) or perovskite.

In one embodiment of the method, the one or more sensing electrodes further comprise a p-type metal oxide selected from the group consisting of nickel(II) oxide (NiO), copper(II) oxide (CuO) and chromium(III) oxide ($Cr_2O_3$).

In one embodiment of the method, measuring a plurality of electric signals from said sensor array comprises measuring the plurality of electric signals when the sensing electrodes are illuminated and measuring the plurality of electric signals when the sensing electrodes are not illuminated.

In one embodiment of the method, response pattern obtained when the sensing electrodes are illuminated and response pattern obtained when the sensing electrodes are not illuminated are different.

In one embodiment of the method, the method measures a wider variety of VOCs as compared to methods in which the sensing electrodes are illuminated or not illuminated throughout the entire process of measurement of electric signals.

In one embodiment of the method, the pattern recognition algorithm includes but is not limited to principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

In one embodiment of the method, a significantly different response pattern of the test sample as compared to that of the control sample is indicative of the existence or stage of the disease.

In one embodiment of the method, the disease is lung cancer, colorectal cancer or heart failure.

In one embodiment of the method, the method further determines subtype of the lung cancer or heart failure.

In one embodiment, the present invention provides a use of a sensor array for detecting a disease in a subject, the use comprises:
 a) exposing the sensor array to a test exhaled breath sample obtained from the subject, the sensor array comprising a plurality of sensing electrodes and a reference electrode;
 b) measuring a plurality of electric signals from the sensor array indicating the presence or concentration of a plurality of volatile organic compounds (VOCs); and
 c) analyzing a response pattern obtained from the plurality of electric signals using a pattern recognition algorithm by comparing it with a response pattern obtained from one or more healthy subject, thereby detecting the disease.

In one embodiment of the use, the VOCs are indicative of the existence or stage of the disease.

In one embodiment of the use, the sensor array is a light-regulated electrochemical sensor.

In one embodiment of the use, each of the VOCs either undergoes an oxidation or reduction when it contacts the sensing electrode, thereby resulting in a flow of electrons between the sensing electrode and reference electrode and generating electric signals.

In one embodiment of the use, each of the sensing electrodes comprises one or more of a photoactive metal oxide and a photoactive metal oxide-based material.

In one embodiment of the use, the photoactive metal oxide is zinc oxide or titanium oxide.

In one embodiment of the use, the photoactive metal oxide-based material is zinc oxide/cerium(IV) oxide ($ZnO/CeO_2$), iron(III) oxide ($Fe_2O_3$), zinc oxide/indium(III) oxide ($ZnO/In_2O_3$), zinc oxide/bismuth(III) oxide ($ZnO/Bi_2O_3$) or perovskite.

In one embodiment of the use, one or more sensing electrodes further comprise a p-type metal oxide such as nickel(II) oxide (NiO), copper(II) oxide (CuO) and chromium(III) oxide ($Cr_2O_3$).

In one embodiment of the use, measuring said plurality of electric signals from the sensor array comprises measuring the plurality of electric signals when the sensing electrodes are illuminated and measuring the plurality of electric signals when the sensing electrodes are not illuminated.

In one embodiment of the use, response pattern obtained when the sensing electrodes are illuminated and response pattern obtained when the sensing electrodes are not illuminated are different.

In one embodiment of the use, the use measures a wider variety of VOCs as compared to uses in which the sensing electrodes are illuminated or not illuminated throughout the entire process of measurement of electric signals.

In one embodiment of the use, the pattern recognition algorithm includes but is not limited to principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

In one embodiment of the use, a significantly different response pattern of the test sample as compared to that of the control sample is indicative of the existence or stage of the disease.

In one embodiment of the use, the disease is lung cancer, colorectal cancer or heart failure.

In one embodiment of the use, the use further determines subtype of the lung cancer or heart failure.

In one embodiment, the present invention provides a system for detecting a plurality of volatile organic compounds (VOCs), the system comprises:
a) a gas collector for introducing a gas sample to the system;
b) a gas chamber for storing the gas sample received from the gas collector;
c) a sensor array comprising a plurality of sensing electrodes and a reference electrode;
d) a light source for illuminating the sensing electrodes;
e) a detection unit for measuring a plurality of electric signals as a result of oxidation or reduction of the VOCs at the sensing electrodes, thereby generating a response pattern indicating the presence or concentration of the VOCs in the gas sample;
f) an analyzer for comparing and analyzing the response pattern obtained from the gas sample with a response pattern obtained from a control sample, thereby providing data indicative of the existence of the plurality of VOCs in the gas sample;
g) a pump for driving the movement of gas sample into and within the system; and
h) a control system for controlling the operation of the system.

In one embodiment of the system, the gas collector comprises a pre-concentrator for concentrating the VOCs in the gas sample and/or a dehumidifying unit for removing water vapour from the gas sample.

In one embodiment of the system, the control system is connected to a plurality of operating sensors and regulators, wherein each of the operating sensors measures one or more operating parameters during the operation and each of said regulators adjusts one or more operating parameters during the operation.

In one embodiment of the system, the system is a wireless system and comprises a data communication chip for wireless communication between the system and a host computer system.

In one embodiment of the system, the presence and/or concentration of the plurality of VOCs is indicative of existence or stage of a disease.

In one embodiment of the system, the system detects a VOC having a concentration in the range of 90-300 parts per billion (ppb) in the gas sample.

In one embodiment of the system, the sensor array is a light-regulated electrochemical sensor.

In one embodiment of the system, each of the sensing electrodes comprises one or more of a photoactive metal oxide and a photoactive metal oxide-based material.

In one embodiment of the system, the photoactive metal oxide is zinc oxide or titanium oxide.

In one embodiment of the system, the photoactive metal oxide-based material is zinc oxide/cerium(IV) oxide ($ZnO/CeO_2$), iron(III) oxide ($Fe_2O_3$), zinc oxide/indium(III) oxide ($ZnO/In_2O_3$), zinc oxide/bismuth(III) oxide ($ZnO/Bi_2O_3$) or perovskite.

In one embodiment of the system, one or more sensing electrodes further comprise a p-type metal oxide such as nickel(II) oxide (NiO), copper(II) oxide (CuO) and chromium(III) oxide ($Cr_2O_3$).

In one embodiment of the system, the reference electrode comprises manganese tetroxide ($Mn_3O_4$) or platinum.

This invention will be better understood by reference to the examples which follow. However, one skilled in the art will readily appreciate that the examples provided are merely for illustrative purposes and are not meant to limit the scope of the invention which is defined by the claims following thereafter.

Throughout this application, it is to be noted that the transitional term "comprising", which is synonymous with "including", "containing" or "characterized by", is inclusive or open-ended, and does not exclude additional, un-recited elements or method steps.

EXAMPLES

Example 1—Fabrication of the Sensor Array

This example describes one embodiment of fabrication of a sensor array for sensing gas molecules such as VOCs.

ZnO-based ($ZnO/CeO_2$, $ZnO/Fe_2O_3$ and $ZnO/In_2O_3$) composites were synthesized via the following steps: ZnO (99%, Sigma, Germany) incorporated with different amount of metallic oxide ($CeO_2$, $Fe_2O_3$ or $In_2O_3$, 99%, Sigma, Germany) was ball milled for 2 h to form a homogeneous composite.

In fabrication of YSZ-based electrochemical sensor array, a 1.5×1.5×0.2 cm YSZ plate was utilized. Commercial $Mn_3O_4$ powder (99%, Sigma, Germany) was thoroughly mixed with α-terpineol and the paste was screen-printed on the surface of YSZ, plate to form a 5×5 mm $Mn_3O_4$-banded electrode. Then, after drying at 130° C. overnight. Finally, YSZ plates with the $Mn_3O_4$ layer were calcined at 1400° C. for 2.5 h in air to form the Mn-based reference electrode (RE). Each of the photoactive sensing materials (ZnO and ZnO-based composites) was applied individually on the surface of YSZ plate to form the oxide layer with similar dimensions to the Mn-based RE. Each fabricated oxide layer was also calcined at high temperature to obtain the photoactive sensing electrodes (SEs), the calcination temperature for the sensor array ranged from 300-1000° C. FIG. 1 shows the photograph of one embodiment of fabricated planar YSZ-based electrochemical sensor array of this invention.

Example 2—Evaluating of the Sensing Behavior of the Sensors

This example describes a method for evaluating the sensing behavior of sensors for detecting various types of gas samples.

Both photoactive-SEs and Mn-based RE of the sensor array were simultaneously exposed to a base gas (air: $N_2$+21 vol. % $O_2$) or a sample gas containing each of various gases (e.g. exhaust gases: CO, $C_3H_6$, NO, in the range of 15-100 ppm; volatile organic compounds (VOCs): toluene, nonan, ethylbenzene, n-hexane, benzene, acetone in the range of 1-4.5 ppm) to evaluate the gas sensing characteristics.

Initially, the sensor array was operated without illumination (light off) and the sensing performance was recorded. Then, the sensing behavior of the sensor was examined with exposure to illumination (light on). The electric potential difference ($\Delta V$, $\Delta V = V_{sample\ gas} - V_{base\ gas}$) between SE and RE was recorded by using a electrometer (34970A, Agilent, USA). The distance between the sensor and LED lamp (380-840 nm, 20 W, Yonglin, China) was about 10 cm and the operating temperature ranged from 400-500° C. Response data derived from the sensor array operated at light off and on were processed by principal component analysis (PCA) pattern recognition algorithm which is implemented by input all the data to IMP software.

Example 3—Detection and Analysis of VOCs Related to Lung Cancer

Breath sample will be collected from the oral cavities of patients suffered from: (i) lung cancer and (ii) control healthy patients and will be analyzed by gas chromatography-mass spectrometry (GC-MS) to identify the specific molecular composition of the diseases samples.

This part of the work will focus on clinical study which will give basic data for relating VOC to lung cancer. A total of 500 patients at the clinics of Hong Kong will be sampled during routine treatment. Participants will be adults (>18 years of age), who will be divided into two groups, according to the results of their initial examination:

1. Patients in good health 2. Patients with diagnosed lung cancer. Patients with unclear medical history (e.g. diabetes) or other environmental (e.g. smoking, alcoholism) that may result in the changes in body VOCs will be excluded. An exhaled air samples will be taken from all patients for VOC analysis by GC-MS. The samples will be collected via air bags and stored at 37° C. for 24 hours, the headspace above the sample will be collected and analyzed by GC-MS. The VOCs in the breath samples will be separated by GC-MS. Unsupervised analysis by multivariate statistics principle component analysis and supervised analysis by partial least-squares model for discriminant analysis will be performed to provisional identify/select disease-specific VOC biomarkers/profiles in exhaled-breath samples. At this point, the unique volatile profile of each patient will be linked with his clinical diagnosis and his analysis results will be analyzed for statistical consistency.

Example 4—Characterization of Lung Cancer Signature Volatile Profiles Via Specific Diagnostic Sensory Array This example describes procedure for sensor adaptation and testing, system integration & miniaturization, data transmission and analysis. A tailor-made sensor array containing 6-8 electrochemical gas sensors based on various novel combination of photoactive sensing materials that have been proven ability to detect VOCs that are specific for lung cancer and/or sub-types of lung cancer is prepared and tested.

Sensing materials design for electrochemical gas sensors will be carried out based on photoactive metal oxides. With respect to photoactive metal oxides, ZnO-based materials (e.g. $ZnO/CeO_2$, $ZnO/In_2O_3$, $ZnO/Bi_2O_3$, etc) show an enhanced catalytic activity upon illumination (even in harsh conditions) that can be exploited for sensing. The sensing properties of these photoactive ZnO-based materials can be modified by the dopants. For instance, ZnO doesn't give any selectivity when sensing VOCs, while the $ZnO/Bi_2O_3$ gives high selectivity to nonane. The design of photoactive ZnO-based materials will be guided by molecular simulation software to increase the affinity towards the relevant volatile molecules. In the present study, ZnO will be doped with p-type metal oxides (e.g. NiO, CuO, $Cr_2O_3$) to favor the adhesion onto the surfaces of target VOCs and increase the photocatalytic activity. These sensors will be prototyped and validated on discrete interdigital electrodes and measured using a laboratory Potentiostat that will resemble the read-out capabilities.

Air samples derived from human breath contain more than 90% of water vapor. Particularly, droplets of water vapor would be adsorbed by sensor and hinder the adsorption of VOCs, limiting the analysis accuracy. Electrochemical sensor usually demonstrates great potential overcoming humidity interfering. Besides, when exposing to VOCs, part of VOCs would be gas-phase converted before they reaching the electrochemical reaction interface. Although the gas-phase conversion will decrease response signal of specific VOCs by decreasing their amount presenting to the electrochemical reaction, it can act like a filter to remove uninterested VOCs. Owing to the gas-phase filtrating effect, electrochemical sensor with well-designed sensing layers would exhibit even better discriminating feature. Note that although gas-phase conversion can filtrate uninterested VOCs, it will more or less decrease the response signal of interested VOCs simultaneously. Thus, design of light-regulated electrochemical sensors discussed in this invention will be adopted for designing lung cancer-specific sensors so that the detection limit, sensitivity and discriminating feature can be remarkably enhanced to meet the criterial of sensing lung cancer VOCs.

In this example, 6-8 sensor parts will be intergrade in one electrochemical sensor array for lung cancer study. This complementary analysis will provide clear input on the transfer of the disease-related VOCs into the sensors via an environmental medium that exists between the measurement system and VOC source, and improve sensor optimization. Since there is no practical possibility to collect a completely non-diluted breath/headspace sample(s), it would be critical to assess the dilution and out-diffusion effects on the VOCs content and to map most common ambient VOCs that will contaminate the breath sample through complementary mass spectroscopy. Some of the ambient VOCs may interfere with detection of breath-originating VOCs, and, therefore, they need to be detected, characterized and taken into an account.

To enhance the long-term stability (durability) of the sensor array, the fabrication procedure of the sensor array will be based on the tap-casting (for electrolyte) and screen-printing techniques (for ZnO-based materials). Besides, in order to obtain the optimal sensing performance, the operational parameters will be optimized. The optimization parameters include the thickness of the photoactive ZnO-based materials (thickness of the sensing layer), operational and calcination temperature of the sensors as well as the photo-power of the illumination will be determined.

Example 5—Clinical Testing of the Artificially Intelligent Sensor Array Aiming Towards Proof of Concept A total of 500 patients treated at the clinics of the Hong Kong local area will take part in this study. A diagnostic array of sensor array specific for lung cancer volatile profiles will be constructed and placed in a diagnostic device. Breath samples will be taken from patients entering the clinic, directly into the device, before an initial clinical checkup is performed. The samples will be analyzed with the device, and the resulting diagnosis will be correlated with the clinical diagnosis of the patient. Due to the extremely non-invasive experimental modality (breathing on a device), no significant obstacles are expected at this point.

With the intension of simplify the air sample collection procedure and online analyzing of the air sample, an online collection and data acquisition machine (prototype machine) will be developed. The prototype machine includes one or more of the following: a breath collector comprising at least one pre-concentrator and a dehumidifying unit, a pump system, a gas chamber, at least one sensor array, a light source, one or more operating sensors and regulators, a data communication chip, a display screen and relevant circuits (including a controlling circuitry for operating the pump and maintaining the regular work of sensor array, a processing circuitry for processing the signals from the sensory arrays) and a single chip microcomputer for managing the device and relevant circuits. The prototype machine is designed for directly collecting air sample and giving the analyzing results within 5 mins.

REFERENCES

1. Mead, M. I.; Popoola, O. A. M.; Stewart, G. B.; Landshoff, P.; Calleja, M.; Hayes, M.; Baldovi, J. J.; McLeod, M. W.; Hodgson, T. F.; Dicks, J.; Lewis, A.; Cohen, J.; Baron, R.; Saffell, J. R., The Use of Electrochemical Sensors for Monitoring Urban Air Quality in Low-cost, High-density Networks. *Sens. Actuators, B* 2013, 70, 186-203.
2. Miura, N.; Sato, T.; Anggraini, S. A.; Ikeda, H.; Zhuiykov, S., A Review of Mixed-potential Type Zirconia-based Gas Sensors. *Ionics* 2014, 20, 901-925.
3. Hossain, M.; Saffell, J. R.; Baron, R., Differentiating $NO_2$ and $O_3$ at Low Cost Air Quality Amperometric Gas Sensors. *ACS Sensors* 2016, 1, 1291-1294.
4. Jin, H.; Huang, Y. J.; Jian, J. W., Plate-like $Cr_2O_3$ for Highly Selective Sensing of Nitric Oxide. *Sens. Actuators, B* 2015, 206, 107-110.
5. Jiang, G. P.; Goledzinowski, M.; Comeau, F. J. E.; Zarrin, H.; Lui, G.; Lenos, J.; Veileux, A.; Liu, G. H.; Zhang, J.; Hemmati, S.; Qiao, J. l.; Chen, Z. W., Electrochemical Gas Sensors: Free-Standing Functionalized Graphene Oxide Solid Electrolytes in Electrochemical Gas Sensors. *Adv. Funct. Mater.* 2016, 26, 1670.
6. Jin, H.; Haick, H., UV regulation of non-equilibrated electrochemical reaction for detecting aromatic volatile organic compounds. *Sens. Actuators, B* 2016, 237, 30-40.
7. Liang, X. S.; Wang, B.; Zhang, H.; Diao, B. F.; Quan, B. F.; Lu, G. Y., Progress in NASICON-based Mixed-potential Type Gas Sensors. *Sens. Actuators, B* 2013, 187, 522-532.
8. Liu, Y. X.; Parisi, J.; Sun, X. C.; Lei, Y., Solid-state Gas Sensors for High Temperature Applications-A Review. *J. Mater. Chem. A* 2012, 2, 9919-9943.
9. Brosha, E. L.; Mukundan, R.; Brown, D. R.; Garzon, F. H., Mixed Potential Sensors Using Lanthanum Manganate and Terbium Yttrium Zirconium Oxide Electrodes. *Sens. Actuators, B* 2002, 87, 47-57.
10, Sato. T.; Ikeda, H.; Miura, N., Mixed-Potential Type Zirconia-Based $NH_3$ Sensor Using $SnO_2$-Disk Sensing-Electrode Attached with Sputtered Au. *ECS Electrochem. Lett.* 2014, 3, B13-B15.
11. Yue Li; Xiaogan Li; Zhaoyun Tang; Tang, Z. N.; Yu, J.; Wang, J., Hydrogen Sensing of the Mixed-potential-type $MnWO_4$/YSZ/Pt sensor. *Sens. Actuators, B* 2015, 206, 176-180.
12. Sato, T.; Breedon, M.; Miura, N., Improvement of Toluene Selectivity via the Application of an Ethanol Oxidizing Catalytic Cell Upstream of a YSZ-Based Sensor for Air Monitoring Applications *Sensors* 2012, 12, 4706-4714.
13. Suetsugu, Y.; Sato, T.; Breedon, M.; Miura, N., $C_3H_6$ Sensing Characteristics of Rod-type Yttria-stabilized Zirconia-based Sensor for ppb Level Environmental Monitoring Applications. *Electrochim. Acta* 2012, 73, 118-122.
14. Mondal, S. P.; Dutta, P. K.; Hunter, G. W.; Ward. B. J.; Laskowski, D.; Dweik, R. A., Development of High Sensitivity Potentiometric $NO_x$ Sensor and Its Application to Breath Analysis. *Sens. Actuators, B* 2011, 158, 292-298.
15. Wang. B.; Liu, F. M.; Yang, X.; Guan, Y. H.; Ma, C.; Hao, X. D.; Liang, X. S.; Liu, F. M.; Sun, P.; Zhang, T.; Lu, G. Y., Fabrication of Well-Ordered Three-Phase Boundary with Nanostructure Pore Array for Mixed Potential-Type Zirconia-Based $NO_2$ Sensor. *ACS Appl. Mater. Inter faces* 2016, 8, 16752-16760.
16. Zhang, J. M.; Su, Y. H.; Zhu, Y. H.; Yun, J. P.; Yang, X. L., Photoelectrochemical Biofuel Cell with Dendrimer-encapsulated CdSe Nanoparticles-sensitized Titanium Dioxide as the Photoanode, *New J. Chem,* 2014, 38, 2300-2304.
17. Hambourger, G. K. M.; Vaughn, M. D.; Moore, G. F.; Gust, D.; Moore, A. L.; Moore, T. A., Solar Energy Conversion in a Photoelectrochemical Biofuel Cell, *Dalton Trans,* 2009, 9979-89.
18. Hongqiu Liang; Xin Zhang; Huihui Sun; Han Jin; Xiaowei Zhang; Qinghui Jin; Jie Zou; Hossam Haick; Jiawen Jian, Light-Regulated Electrochemical Sensor Array for Efficiently Discriminating Hazardous Gases, *ACS Sens.,* 2017, 2, 1467-1473.
19, Agarwal, S. M.; Sharma, M.; Fatima, S., VOCC: A Database of Volatile Organic Compounds in Cancer, *RSC Adv.* 2016, 6, 114783-114789.
20. Poli, D.; Carbognani, P.; Corradi, M.; Goldoni, M.; Acampa, O.; Balbi, B.; Bianchi, L.; Rusca, M.; Mutti, A., Exhaled volatile organic compounds in patients with non-small cell lung cancer: cross sectional and nested short-term follow-up study, *Resp. Res.* 2005, 6, 71-81.
21, Peng, G.; Tisch, U.; Adams, O.; Hakim, M.; Shehada, N.; Broza, Y. Y.; Billan, S.; Abdah-Bortnyak, R.; Kuten, A.; Haick, H., Diagnosing lung cancer in exhaled breath using gold nanoparticles, *Nat. Nanotech* 2009, 4, 669-673.
22. Di Lena M, Porcelli F, Altomare D F. Volatile organic compounds as new biomarkers for colorectal cancer: a review. Colorectal Dis. 2016 July; 18(7):654-63.

23. Fabiana G, Marcondes-Braga et al., Exhaled Breath Analysis in Heart Failure. Curr Heart Fail Rep. 13(4), 166-71

What is claimed is:

1. A method for preparing an electrochemical sensor based on light regulated electrochemical reaction, wherein:
said electrochemical sensor based on light regulated electrochemical reaction comprises a YSZ solid electrolyte layer, a heating plate, a reference electrode and three sensing electrodes;
said YSZ solid electrolyte layer and said heating plate are cube-shaped, and said YSZ solid electrolyte layer has a side length equal to a side length of said heating plate;
said YSZ solid electrolyte layer has a bottom surface attached and fixed to a top surface of said heating plate;
said reference electrode and said three sensing electrodes are all cubes of same size;
said reference electrode and said three sensing electrodes are spaced apart on a top surface of said YSZ solid electrolyte layer;
each of said reference electrode and said three sensing electrodes has a bottom surface respectively attached and fixed to said top surface of the YSZ solid electrolyte layer, and each of said reference electrode and said three sensing electrodes has a center point, wherein said reference electrode and said three sensing electrodes are arranged with their center points forming a square that is concentric with said top surface of the YSZ solid electrolyte layer;
said three sensing electrodes are a first sensing electrode, a second sensing electrode and a third sensing electrode respectively;
said first sensing electrode is made of zinc oxide;
said second sensing electrode is made of a mixture of zinc oxide and iron (III) oxide, wherein said iron (III) oxide has a mass 20% of said zinc oxide in said mixture of zinc oxide and iron (III) oxide;
said third sensing electrode is made of a mixture of zinc oxide and cerium oxide, wherein said cerium oxide has a mass 30% of said zinc oxide in said mixture of zinc oxide and cerium oxide;
said reference electrode is made of manganese dioxide;
said reference electrode is located between said first sensing electrode and said third sensing electrode;
said second sensing electrode is located between said first sensing electrode and said third sensing electrode;
a reference electrode lead wire is provided on said reference electrode;
a first sensing electrode lead wire is provided on said first sensing electrode;
a second sensing electrode lead wire is provided on said second sensing electrode; and
a third sensing electrode lead wire is provided on said third sensing electrode;
wherein said preparation method comprises the steps of:
(1) preparing said YSZ solid electrolyte layer and said heating plate;
(2) mixing terpineol and ethyl cellulose at a mass ratio of 94:6 to form a terpineol slurry;
(3) mixing manganese dioxide powder and said terpineol slurry in an agate mortar at a mass ratio of 1:1.5 to form a first slurry;
(4) using silk-screen printing technology to print said first slurry on the top surface of said YSZ solid electrolyte layer to obtain a first product with a first slurry layer;
(5) putting the first product obtained from step (4) into a dry box to dry at 130° C. for 12 hours, before placing it in a sintering furnace to sinter at 1400° C. for 2 hours and cooling to room temperature, and said reference electrode is formed from said first slurry layer on said top surface of said YSZ solid electrolyte layer;
(6) mixing zinc oxide and said terpineol slurry at a mass ratio of 1:1.5 in an agate mortar to form a second slurry;
(7) using silk-screen printing technology to print said second slurry on said top surface of said YSZ solid electrolyte layer to obtain a second product with a second slurry layer;
(8) putting the second product obtained from step (7) into a dry box to dry at 130° C. for half an hour, before removing said second product from the dry box and cooling to room temperature to form said first sensing electrode from said second slurry layer on said top surface of said YSZ solid electrolyte layer;
(9) weighing zinc oxide powder and iron (III) oxide powder to form a mixture with mass ratio of 5:1, and mixing the mixture of zinc oxide powder and iron (III) oxide powder with said terpineol slurry in an agate mortar to obtain a third slurry, wherein the mixture of said zinc oxide powder and iron (III) oxide powder to said terpineol slurry is at a mass ratio of 1:1.5;
(10) using silk-screen printing technology to print said third slurry on said top surface of said YSZ solid electrolyte layer to obtain a third product with a third slurry layer;
(11) putting the third product obtained from step (10) into a dry box to dry at 130° C. for half an hour, before removing said third product from the dry box and cooling to room temperature to form said second sensing electrode from said third slurry layer on said top surface of said YSZ solid electrolyte layer;
(12) weighing zinc oxide powder and cerium oxide powder to form a mixture with mass ratio of 10:3, and mixing said mixture of zinc oxide powder and cerium oxide powder with said terpineol slurry in an agate mortar to obtain a fourth slurry, wherein said mixture of zinc oxide powder and cerium oxide powder to said terpineol slurry is at a mass ratio of 1:1.5;
(13) using silk-screen printing technology to print said fourth slurry on said top surface of said YSZ solid electrolyte layer to obtain a fourth product with a fourth slurry layer;
(14) forming a fifth product by dispensing a Pt slurry on each of said reference electrode, said first sensing electrode, said second sensing electrode and said fourth slurry layer, and then drawing out a lead wire from each of said Pt slurry to form said reference electrode lead, said first sensing electrode lead, said second sensing electrode lead and said third sensing electrode lead that is electrically connected to said reference electrode, said first sensing electrode, said second sensing electrode and said third sensing electrode respectively;
(15) forming a sixth product by putting the fifth product obtained from step (14) into a dry box to dry at 130° C. for 12 hours, removing said fifth product from said dry box and putting it in a sintering furnace to sinter at 900° C. for 2 hours, removing it from said sintering furnace and cooling to room temperature to form said third sensing electrode from said fourth slurry layer; and

(16) placing said heating plate under said YSZ solid electrolyte layer of the sixth product obtained from step (15), pasting said heating plate and said YSZ solid electrolyte layer together with a high temperature resistant adhesive to complete the sensor preparation.

2. The method of claim 1, wherein said heating plate is made of alumina.

3. The method of claim 1, wherein:
said YSZ solid electrolyte layer has a length of l cm;
said YSZ solid electrolyte layer has a width of d cm;
said YSZ solid electrolyte layer has a thickness of h mm;
said heating plate has a length of l cm;
said heating plate has a width of d cm;
said heating plate has a thickness of $h_1$ mm; wherein
value of l ranges from 1.3 cm to 1.7 cm;
value of d ranges from 1.3 cm to 1.7 cm;
value of h ranges from 1 mm to 3 mm;
value of $h_1$ ranges from 1.1 mm to 1.5 mm; and
each of said reference electrode, said first sensing electrode, said second sensing electrode, and said third sensing electrode has a length of $l_1$;
each of said reference electrode, said first sensing electrode, said second sensing electrode and said third sensing electrode has a width of $d_1$; and
each of said reference electrode, said first sensing electrode, said second sensing electrode and said third sensing electrode has a thickness of $h_2$; wherein
value of $l_1$ ranges from 4 mm to 6 mm;
value of $d_1$ ranges from 4 mm to 6 mm; and
value of $h_2$ ranges from 14 μm to 16 μm.

* * * * *